US012797591B2

(12) United States Patent
Blain Christen et al.

(10) Patent No.: US 12,797,591 B2
(45) Date of Patent: Nov. 17, 2026

(54) SYSTEMS AND METHODS FOR IMPLANTABLE SELF-MONITORING SYSTEMS TO DETECT PRESSURE AND FLOW CHARACTERISTICS

(71) Applicants: Jennifer Blain Christen, Tempe, AZ (US); Daniel Gulick, Tempe, AZ (US); Sule Ozev, Phoenix, AZ (US)

(72) Inventors: Jennifer Blain Christen, Tempe, AZ (US); Daniel Gulick, Tempe, AZ (US); Sule Ozev, Phoenix, AZ (US)

(73) Assignee: Arizona Board of Regents on Behalf of Arizona State University, Tempe, AZ (US)

( * ) Notice: Subject to any disclaimer, the term of this patent is extended or adjusted under 35 U.S.C. 154(b) by 371 days.

(21) Appl. No.: 18/542,080

(22) Filed: Dec. 15, 2023

(65) Prior Publication Data

US 2024/0198064 A1 Jun. 20, 2024

Related U.S. Application Data

(60) Provisional application No. 63/387,596, filed on Dec. 15, 2022.

(51) Int. Cl.
*A61M 27/00* (2006.01)
*G16H 40/63* (2018.01)

(52) U.S. Cl.
CPC .......... *A61M 27/006* (2013.01); *G16H 40/63* (2018.01); *A61M 2205/3334* (2013.01);
(Continued)

(58) Field of Classification Search
CPC ........ A61M 27/006; A61M 2205/3334; A61M 2205/3375; A61M 2205/502; A61M 2205/583; A61M 2205/702; G16H 40/63
(Continued)

(56) References Cited

U.S. PATENT DOCUMENTS 6,170,078 B1 * 1/2001 Erle ............... G01R 31/318342 716/136
7,447,619 B2 * 11/2008 Bartley ................ G06F 30/367 703/2
(Continued)

FOREIGN PATENT DOCUMENTS

CN 119278059 A * 1/2025 ........ A61M 39/0247
EP 2990706 A1 * 3/2016 ......... F16K 37/0083

OTHER PUBLICATIONS

Krishnan et al., Continuous, noninvasive wireless monitoring of flow of cerebrospinal fluid through shunts in patients with hydrocephalus, npj Digital Medicine (2020) 29 (Year: 2020).*
(Continued)

*Primary Examiner* — Stephanie E Bloss
*Assistant Examiner* — Kevin C Butler
(74) *Attorney, Agent, or Firm* — Polsinelli PC

(57) ABSTRACT

A valve device monitoring system for at-home human-in-the-loop hydrocephalus shunt monitoring detects degradation and imminent failure of implantable devices for the treatment of hydrocephalus. Potential mechanisms for failure are presented and associated with observable parameters. The valve device monitoring system enables at-home testing using a non-invasive monitoring methodology. Development of a behavioral model of the valve device monitoring system involves a tightly-coupled valve design and behavioral characterization process aimed at reducing unnecessary monetary, material, animal welfare, and computational costs.

20 Claims, 28 Drawing Sheets

(52) U.S. Cl.
CPC ............... *A61M 2205/3344* (2013.01); *A61M 2205/3375* (2013.01); *A61M 2205/502* (2013.01); *A61M 2205/583* (2013.01); *A61M 2205/702* (2013.01)

(58) Field of Classification Search
USPC .......................................................... 73/865.8
See application file for complete search history.

(56) References Cited

U.S. PATENT DOCUMENTS

| | | | | |
|---|---|---|---|---|
| 8,954,306 | B2 * | 2/2015 | Li | G06F 30/30 703/4 |
| 9,141,915 | B2 * | 9/2015 | Alonso | G06N 3/08 |
| 9,842,177 | B1 * | 12/2017 | Sun | G06F 30/20 |
| 9,851,019 | B2 * | 12/2017 | Shields | F16K 37/0083 |
| 9,852,245 | B2 * | 12/2017 | Kusko | G06F 30/367 |
| 10,016,135 | B2 * | 7/2018 | Wolf, II | A61B 5/0077 |
| 10,297,558 | B1 * | 5/2019 | Shieh | G01R 31/30 |
| 11,038,768 | B1 * | 6/2021 | Madrigal | H04L 25/03057 |
| 2008/0097550 | A1 * | 4/2008 | Dicks | A61N 1/37282 607/59 |
| 2009/0112769 | A1 * | 4/2009 | Dicks | H04L 9/3231 600/301 |
| 2012/0004896 | A1 * | 1/2012 | Li | G06F 30/30 700/121 |
| 2014/0338663 | A1 * | 11/2014 | Pirzada | A61B 5/1112 128/204.23 |
| 2014/0358581 | A1 * | 12/2014 | Sudharsan | G16H 50/20 705/2 |
| 2017/0199946 | A1 * | 7/2017 | Kusko | G06F 30/367 |
| 2019/0012247 | A1 * | 1/2019 | Bullough | G06F 11/26 |
| 2021/0241915 | A1 * | 8/2021 | Singer | G06F 17/11 |
| 2023/0395220 | A1 * | 12/2023 | Vallery | G06T 13/40 |
| 2024/0214079 | A1 * | 6/2024 | Guo | H04B 17/0085 |
| 2024/0339181 | A1 * | 10/2024 | Hompesch | G16H 10/20 |

OTHER PUBLICATIONS

Aralar et al., Assessment of Ventriculoperitoneal Shunt Function Using Ultrasound Characterization of Valve Interface Oscillation as a Proxy. Cureus 10(2): e2205. DOI 10.7759/cureus.2205, Feb. 19, 2018 (Year: 2018).*

Lee et al., Hydrogel Check-Valves for the Treatment of Hydrocephalic Fluid Retention with Wireless Fully-Passive Sensor for the Intracranial Pressure Measurement, Gels 2022, 8, 276. https://doi.org/10.3390/gels8050276 (Year: 2022).*

Kaestner et al, can hear my shunt-audible noises associated ,vith CSF shunts in hydrocephalic patients , Acta Neurochir (2017) 159 :981-986 DOI 10.1007/s00701-017-3179-z (Year: 2017).*

Reddy et al., Long-Term Outcomes of Ventriculoperitoneal Shunt Surgery in Patients with Hydrocephalus, World Neurosurgery, http:/dx.doi.org/10.1016/j.wneu.2013.01.096, World Neurosurg. (2014) 81, 2:404-410. (Year: 2014).*

Bluestein et al., Utilizing Computational Fluid Dynamics in Cardiovascular Engineering and Medicine—What You Need to Know. Its Translation to the Clinic/Bedside, Artif Organs. Feb. 2017 ; 41(2): 117-121. doi:10.1111/aor. 12914. (Year: 2017).*

Hose et al., Cardiovascular models for personalised medicine: Where now and where next?, Medical Engineering and Physics 72 (2019) 38-48 (Year: 2019).*

Aralar A, Bird M, Graham R, Koo B, Chitnis P, Sikdar S, Shenai M. "Assessment of Ventriculoperitoneal Shunt Function Using Ultrasound Characterization of Valve Interface Oscillation as a Proxy" Cureus. Feb. 19, 2018; 10(2).

Czosnyka Z, Czosnyka M, Richards HK, Pickard JD. Posture-related overdrainage: comparison of the performance of 10 hydrocephalus shunts in vitro. Neurosurgery. Feb. 1998;42(2):327-33; discussion 333-4.

Gulick, D., Jung, Y., Lee, S., Ozev, S., Christen, J.B., "Exploring Model-based Failure Prediction of Passive Bio-electro-mechanical Implants," 2022 IEEE 40th VLSI Test Symposium, 7 pages.

Kaestner, S., Fraij, A., Deinsberger, W., Roth, C, "I can hear my shunt-audible noises associated with CSF shunts in hydrocephalic patients," Acta Neurochir, Apr. 14, 2017, 159:981-986, 6 pages.

Krishnan, S.R., et al., "Continuous, noninvasive wireless monitoring of flow of cerebrospinal fluid through shunts in patients with hydrocephalus," NPJ/Digital Medicine, 2020, 3:29, 11 pages.

S. Lee, S. Liu, R. Bristol, M.C. Preul, J. Chae, J. Blain Christen. "Hydrogel Check-Valves for the Treatment of Hydrocephalic Fluid Retention with Wireless Fully-Passive Sensor for the Intracranial Pressure Measurement". Unpublished (in review), MDPI Journal, Gels, 2022, 8:276, 14 pages.

Levrini V, Czosnyka Z, Lawes I, Kolias AG, Mannion R. "Shunt Testing In Vivo: Illustration of Partially Obstructed Ventricular Catheter by In-Growing Choroid Plexus," Cureus. Jul. 19, 2020;12(7), 5 pages.

Reddy, G. Kesava, Papireddy Bollam, and Gloria Caldito. "Long-term outcomes of ventriculoperitoneal shunt surgery in patients with hydrocephalus." World neurosurgery 81.2 (2014): 404-410, 7 pages.

H. N. Schwerdt et al., "A Fully Passive Wireless Microsystem for Recording of Neuropotentials Using RF Backscattering Methods," in Journal of Microelectromechanical Systems, vol. 20, No. 5, pp. 1119-1130, Oct. 2011, 12 pages.

Stone, Jonathan J., et al. "Revision rate of pediatric ventriculoperitoneal shunts after 15 years." Journal of Neurosurgery: Pediatrics 11.1 (2013): 15-19, 5 pages.

* cited by examiner (a) Existing Product Design and Use Cycle (b) Proposed Design and Test Cycle Duckbill valve failure modes Operational: curved valve seat A.

B.

Failure: flat valve seat C.

D.

Channel profile variations (top-down view)

SYSTEMS AND METHODS FOR IMPLANTABLE SELF-MONITORING SYSTEMS TO DETECT PRESSURE AND FLOW CHARACTERISTICS

CROSS-REFERENCE TO RELATED APPLICATIONS

The present application claims priority from U.S. Provisional Patent Application No. 63/387,596 filed Dec. 15, 2022, which is incorporated herein by reference in its entirety.

FIELD

The present disclosure generally relates to monitoring pressure and flow characteristics of biofluids, and in particular, to implantable self-monitoring systems and associated methods for monitoring pressure and flow characteristics of biofluids.

BACKGROUND

Hydrocephalus is an excessive buildup of pressure due to excess cerebrospinal fluid (CSF) in the intracranial space that surrounds the brain, due to a blockage or insufficiency in the natural drainage system. Standard treatment is the placement of a shunt, a length of tubing inserted into the brain to release the excess fluid. Shunts include a valve to regulate pressure and prevent backflow.

Unfortunately, 40-50% of shunts fail within the first two years after placement and must be surgically repaired or replaced. Frequent complications include mechanical failure of the tubing or valve, clogging of the inlet or outlet by tissue, and parametric failures including overdrainage and underdrainage. Modern shunts may include externally-adjustable programmable valves, but these still are generally adjusted based on clinically observed symptoms. Shunt failure may be total or intermittent, and associated symptoms may be overt or may be subtle and nonspecific (e.g. headache).

Evaluation of shunts after placement is challenging. Imaging (MRI or ultrasound) can observe secondary effects (e.g. enlargement or collapse of the fluid-filled ventricles within the brain), but cannot directly measure pressure or flow. Infusion studies may be performed by injecting fluid through the scalp into a shunt reservoir outside the skull and measuring the pressure created by this volume infusion. While this is a minimally-invasive procedure, it does require a clinic visit.

Design automation and built-in self-test (BIST) methods have dramatically improved the reliability of microelectronic devices. These techniques have been studied and refined over several decades, however, they are generally confined to the field of microelectronics. The present disclosure outlines extension of these techniques to bio-mechanical medical devices, beginning with an exemplary device with high failure rates: implanted biofluid valves. Currently, valve failure is only observed after symptoms arise and the device is surgically removed. In addition to causing potential harm to patients and increasing the healthcare burden, this practice severely limits the information that can be obtained regarding the degradation and failure of the devices.

Adapting design automation and built-in self-test methods to valve implants requires significant modification due to the differences in function and failure between microelectronics in the ambient environment vs. mechanical valves in a biological environment. Furthermore, the type of testing that can be performed as a built-in self-test with human-in-the-loop will necessarily have different constraints than a classic BIST.

The present disclosure provides a model of the relationship between design parameters and performance, in terms of functional performance, as well as reliability and lifetime of a device. The model informs a more generalized approach to an automated design flow for implants for a given set of specifications. The methods outlined herein iterate on the relationship between model parameters as devices are fabricated and tested both on the bench and in animal models. This process provides a systematic approach to modeling and designing implantable devices based on a given set of specifications.

It is with these observations in mind, among others, that various aspects of the present disclosure were conceived and developed.

SUMMARY

A valve monitoring system includes: a sensor that generates a signal expressive of indirect operational characteristics of a valve device, the valve device being positioned between a first cavity and a second cavity of a bodily system for facilitating drainage of a fluid from the first cavity to the second cavity; and a processor in communication with a memory and the sensor. The memory can include instructions executable by the processor to: access signal data indicative of the signal generated by the sensor; compare the signal data to a behavioral model associated with the valve device, the behavioral model connecting the indirect operational characteristics of the valve device expressed by the signal data with a parametric behavior characteristic of the valve device with respect to the bodily system; and infer a value of the parametric behavior characteristic of the valve device based on a comparison between the signal data and the behavioral model.

The indirect operational characteristics of the valve device can include one or more of: an opening time of the valve device associated with an opening action of the valve device over one or more cycles; a closing time of the valve device associated with a closing action of the valve device over the one or more cycles; and a flow rate of the fluid through the valve device over the one or more cycles. The parametric behavior characteristics of the valve device can include one or more of: an intracavity pressure associated with the first cavity over one or more cycles; a cracking pressure of the valve device; and a reverse flow rate associated with backflow of the fluid from the second cavity to the first cavity over the one or more cycles.

The sensor can be selected from: an acoustic sensor that generates the signal upon audio detection of an opening action or a closing action of the valve device; and an ultrasound sensor that generates the signal expressive of the fluid flow through the valve device; where the signal is readable by a computing system upon interrogation of the sensor.

The memory can further include instructions executable by the processor to: infer, based on the value of the parametric behavior characteristic of the valve device and based on the behavioral model, a type of operational state of the valve device; and infer, based on the value of the parametric behavior characteristic of the valve device and based on the behavioral model, a remaining lifetime of the valve device.

Further, the memory can further include instructions executable by the processor to: prompt, by an interface in communication with the processor, a user of the valve device to perform the series of postural changes; access the signal data indicative of the signal generated by the sensor upon performance of the series of postural change; correlate the indirect operational characteristics of the valve device over one or more cycles with a series of postural changes associated with the bodily system; and compare, in view of correlation between the indirect operational characteristics and the series of postural changes, the behavioral model connecting the indirect operational characteristics of the valve device expressed by the signal data with parametric behavior characteristics of the valve device with respect to the bodily system.

The memory can also include instructions executable by the processor to: construct, based on the value of the parametric behavior characteristic of the valve device and based on the behavioral model, a graphic for display at a display device in communication with the processor that shows the indirect operational characteristics of the valve device and the value of the parametric behavior characteristic of the valve device with respect to time.

A method of inferring a value of a parametric behavior characteristic that indicates function of a valve device using a behavioral model of the valve device can include: accessing signal data indicative of a signal generated by a sensor, the signal being expressive of one or more indirect operational characteristics of a valve device, the valve device being positioned between a first cavity and a second cavity of a bodily system for facilitating drainage of fluid from the first cavity to the second cavity; comparing the signal data to a behavioral model associated with the valve device, the behavioral model connecting the one or more indirect operational characteristics of the valve device expressed by the signal data with one or more parametric behavior characteristics associated with the valve device with respect to the bodily system; and inferring a value of a parametric behavior characteristic of the one or more parametric behavior characteristics associated with the valve device based on comparison between the signal data and the behavioral model. The method can further include: correlating the one or more indirect operational characteristics of the valve device over one or more cycles with a series of postural changes associated with the bodily system; and comparing, in view of correlation between the one or more indirect operational characteristics and the series of postural changes, the behavioral model connecting the one or more indirect operational characteristics of the valve device expressed by the signal data with parametric behavior characteristics of the valve device with respect to the bodily system.

The one or more indirect operational characteristics of the valve device can include one or more of: an opening time of the valve device associated with an opening action of the valve device over one or more cycles; a closing time of the valve device associated with a closing action of the valve device over the one or more cycles; and a flow rate of fluid through the valve device over the one or more cycles.

The one or more parametric behavior characteristics of the valve device can include one or more of: an intracavity pressure associated with the first cavity over one or more cycles; a cracking pressure of the valve device; and a reverse flow rate associated with backflow of fluid from the second cavity to the first cavity over the one or more cycles.

A method of developing a behavioral model for use in inferring a value of a parametric behavior characteristic that indicates function of a valve device can include: measuring, by a plurality of sensors associated with a valve device implanted within an animal bodily system over a plurality of cycles, a set of operational characteristics associated with the valve device. The set of operational characteristics associated with the valve device can include: an intracavity pressure associated with a first cavity of the animal bodily system; and a set of indirect operational characteristics of the valve device, including timestamps associated with an opening action of the valve device or a closing action of the valve device over the plurality of cycles, and fluid flow through the valve device. Further, the method can include constructing a behavioral model for the valve device representing connections between the intracavity pressure and the set of indirect operational characteristics of the set of operational characteristics. The behavioral model can express a correlation between the set of operational characteristics and a series of postural changes exhibited by the animal bodily system.

Further, the behavioral model can incorporate an equivalent circuit behavioral model in terms of an equivalent circuit model of the valve device and the animal bodily system, the equivalent circuit behavioral model representing connections between one or more design parameters of the valve device, one or more bodily system parameters including intracavity pressure, and one or more equivalent circuit parametric behavioral characteristics of the valve device. The method can further include: simulating operation of the equivalent circuit model of the valve device; varying one or more bodily system parameters of the equivalent circuit model; observing, based on simulated operation of the equivalent circuit model of the valve device, one or more equivalent circuit parametric behavioral characteristics of the equivalent circuit model responsive to variation of the one or more bodily system parameters; and correlating the one or more bodily system parameters of the equivalent circuit model with the one or more equivalent circuit parametric behavioral characteristics of the valve device of the equivalent circuit model. The behavioral model can incorporate connections between the equivalent circuit behavioral model and the set of operational characteristics associated with the valve device and the animal bodily system.

The behavioral model can also incorporate a testbed behavioral model in terms of a testbed model of the valve device and the animal bodily system, the testbed behavioral model representing connections between one or more design parameters of the valve device, one or more bodily system parameters including intracavity pressure, and one or more testbed parametric behavioral characteristics of the valve device based on the testbed model. As such, the method can further include: simulating operation of the testbed model of the valve device; varying the one or more bodily system parameters of the testbed model; measuring the one or more testbed parametric behavioral characteristics of the valve device of the testbed model responsive to variation of the one or more bodily system parameters; and correlating the one or more bodily system parameters of the testbed behavioral model with the one or more testbed parametric behavioral characteristics of the valve device of the testbed model. The behavioral model can incorporate connections between the testbed behavioral model and the set of operational characteristics associated with the valve device and the animal bodily system, and can also incorporate connections between the testbed behavioral model and an equivalent circuit behavioral model.

BRIEF DESCRIPTION OF THE DRAWINGS

For purposes of illustrating and exemplifying the claimed invention, the drawings show aspects of embodiments of the present disclosure. However, it should be understood that the claimed invention is not limited to the exact arrangement and means of exemplary embodiments shown in the drawings.

FIGS. 19A and 19B show schematic representation of a valve operation mechanism, illustrating its open and closed states based on the cracking pressure in relation to the pressure difference between the inlet and outlet sides, and where FIG. 19C shows pressure-flow rate relationships to evaluate valve behavior while varying parameters including bill length and fluid channel width.

FIG. 20A shows simulation of fluid velocity (color scale) and valve material stress (grayscale) for simulated CSF flow, and where FIG. 20B shows a photomicrograph of a valve post-failure, showing hydrogel detached from the surrounding support.

FIGS. 21A-21C are graphical representations showing behavior result characterization of various design parameters and where FIGS. 21D-21G illustrate possible channel profile variations for a valve device.

Corresponding reference characters indicate corresponding elements among the view of the drawings. The headings used in the figures do not limit the scope of the claims.

DETAILED DESCRIPTION

Figure 1A:
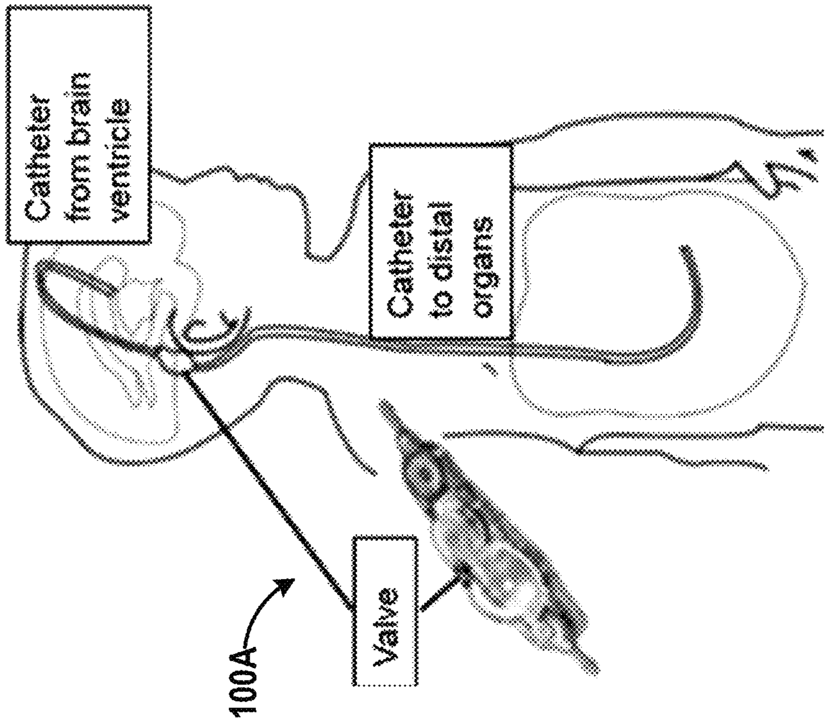
FIG. 1A is a diagram illustrating a conventional valve system implanted within a body for drainage of fluid between a first cavity and a second cavity.

The present disclosure outlines systems and methods for monitoring in vivo valve functionality with minimally-invasive measurement methods. A valve device monitoring system includes one or more sensors that can generate signals expressive of indirect operational characteristics that can be used to infer behavior of a valve device, such as timestamps for opening actions and closing actions of the valve device, or characterizing fluid flow though the valve device. Based on the indirect operational characteristics, a computing device in communication with the one or more sensors can infer values of one or more parametric behavior characteristics of the valve device, such as cracking pressure and reverse flow, based on a behavioral model for the valve device. The behavioral model can correlate values of the indirect operational characteristics with values of the one or more parametric behavior characteristics based on correlations therebetween from in-vitro and in-vivo testing of the valve device.

1. Behavioral Model and Purpose Overview

In a primary embodiment, the behavioral model for the valve device is developed by observing and correlating behavior of in-vitro models including an equivalent circuit behavioral model and a testbed behavioral model, and further developed by correlating in-vitro behavior with in-vivo behavior from animal testing. In a further aspect, development and refinement of the behavioral model can be accomplished in tandem with development and refinement of the valve device. Following development and refinement of the behavioral model, the valve device monitoring system can be deployed for use in humans for monitoring functionality of the valve device.

Rather than taking direct measurement of the parametric behavior characteristics, the valve monitoring system outlined herein aims to measure and correlate indirect operational characteristics with the parametric behavior characteristics at deployment. The reason for this is to avoid invasive procedures, design choices, and complications associated with direct measurement of the parametric behavior characteristics. For example, intracavity pressure (ICP) is one important value in monitoring valve device function that quantifies a pressure associated with a first cavity from which fluid is being drained (such as a cranium, in which case ICP would be more specifically referred to as "intracranial pressure). A valve device that is functioning properly should have a "cracking pressure" that is within a specified range. When ICP reaches the cracking pressure, the valve device should open to relieve excess pressure within the first cavity. When ICP starts to fall below the cracking pressure, the valve device should close to prevent excessive fluid drainage. One marker of poor function of a valve device can be a change in cracking pressure from the intended range, usually due to a mechanical failure, blockage, or degradation of the valve device. Such a change may be subtle, and is often not caught until a catastrophic failure occurs. To evaluate the cracking pressure of a valve device that is implanted within a body, the ICP over time may be plotted. However, direct measurement of ICP requires implanting pressure sensors in association with the first cavity, which can be risky. Further problems are encountered when considering methods for powering or interrogating implanted pressure sensors, particularly those implanted within a cranium. As such, there is a need to examine valve function with indirect, minimally-invasive methods.

2. Valve Device Examples

Figure 1B:
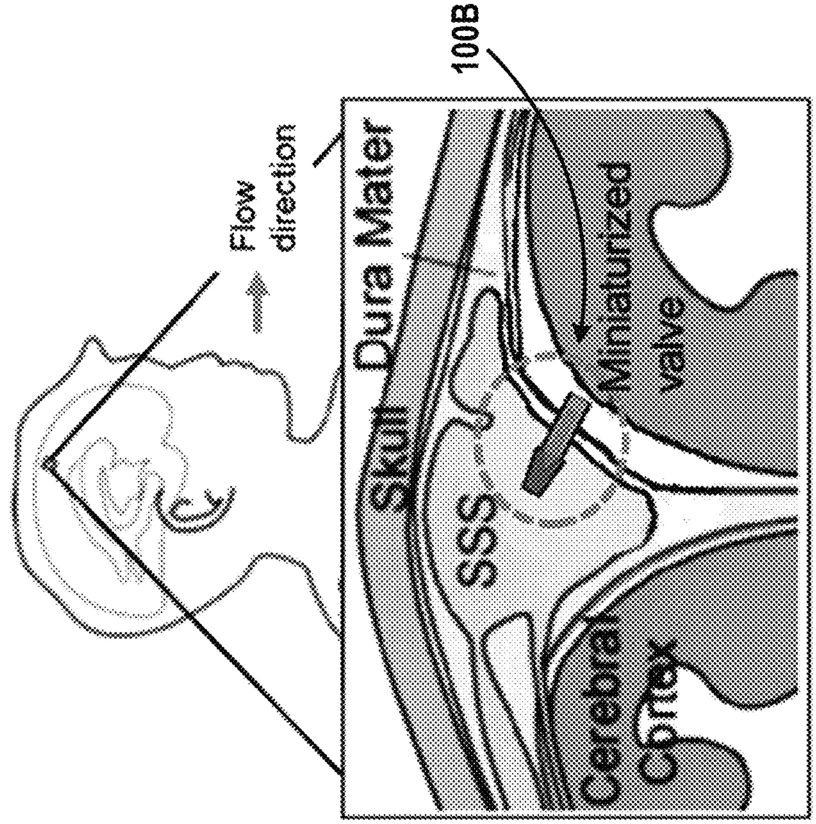
FIG. 1B is a diagram illustrating a miniaturized valve system implanted within a body for drainage of fluid between a first cavity and a second cavity.

FIGS. 1A and 1B show two example valve devices 100A and 100B implanted within a human for treatment of hydrocephalus that are used for illustration throughout, e.g., to be monitored by a valve monitoring system outlined herein. As shown, the valve device 100A or 100B can be a one-way valve between a first cavity and a second cavity.

3. Valve Monitoring System Overview

One example implementation of a valve device monitoring system (e.g., "monitoring system 200") is shown in FIG. 2 for monitoring function of a valve device (e.g., valve device 100B discussed above and shown as an example in FIG. 2). The monitoring system 200 can be computer-implemented (e.g., at a computing device 204), and can include valve monitoring processes/services 310 which can be a software or software suite that can run on computing device 204. The monitoring system 200 can access signal data 302 that carries information about indirect operational characteristics 312 from one or more sensors, which can include an ultrasound sensor 202A and/or an acoustic sensor 202B. The one or more sensors generate signals that are readable by the computing device 204 as signal data 302 upon interrogation of the sensor. The indirect operational characteristics 312 can include timestamps associated with opening and closing actions of the valve device (e.g., measured by the acoustic sensor 202B) and quantitative or qualitative characteristics of fluid flow through the valve device (e.g., measured by the ultrasound sensor 202A). Other sensor modalities that may be suitable for measuring quantitative or qualitative characteristics of fluid flow through the valve device can include passive RF backscatter, among others.

The ultrasound sensor 202A may be positioned external to the body for obtaining ultrasound data. The ultrasound sensor 202A may be a standard ultrasound sensor that a clinician may use to interrogate the valve device. The acoustic sensor 202B may be implanted within the body, but may be implanted at a position near the valve device at the discretion of a practitioner. In some examples, such as when the valve device is within the cranium, the acoustic sensor 202B may be implanted underneath the skin but exterior to the cranium. In other examples, when appropriate and feasible, the acoustic sensor 202B may be within the cranium. The acoustic sensor 202B can record or otherwise monitor audio signals associated with opening and closing of the valve device.

In some examples, it may be necessary or helpful to induce posture changes that will cause the valve device to open or close as ICP and other factors change. The computing device 204 may prompt a user to perform a sequence of posture changes to check functionality of the valve device under certain conditions. As such, the one or more sensors can include a posture sensor 202C that can measure posture or motion signal data 304, which the monitoring system 200 can interpret as posture information 314. The monitoring system 200 can correlate posture information 314 with the indirect operational characteristics 312 in order to better understand how the valve device is functioning in view of induced posture changes. As the indirect operational characteristics 312 can be time-dependent, it is important to examine how the valve device responds to the induced posture changes.

The monitoring system 200 can apply the indirect operational characteristics 312 and posture information 314 as input to a behavioral model 320 that compares patterns and values of indirect operational characteristics 312 over a plurality of cycles with those found during in-vitro and in-vivo testing, and connect the indirect operational characteristics 312 with parametric behavior characteristics found during in-vitro and in-vivo testing. The posture information 314 serves as contextual information that accompanies the indirect operational characteristics 312. Based on the comparison, the behavioral model 320 enables the monitoring system 200 to infer values of parametric behavior characteristics 332 associated with the valve device and a bodily system, such as ICP, cracking pressure, and reverse flow in view of the indirect operational characteristics 312. These (inferred) values of parametric behavior characteristics 332 can be used to infer an operational state of the valve device, which can range from "functional" to various types of "parametric failure" to various types of "catastrophic failure", enabling practitioners to diagnose and treat problems sooner.

During in-vitro and in-vivo testing, values of parametric behavior characteristics 332 can be directly measured and correlated with indirect operational characteristics 312 that would be measured during deployment using minimally-invasive sensing modalities. Additional correlations can also be made between design parameters of a valve device and resultant effects on behavior, which can help enable adaptation of behavioral models 320 to different valve devices and bodily systems, or can otherwise enable refinement of valve designs.

Figure 10:
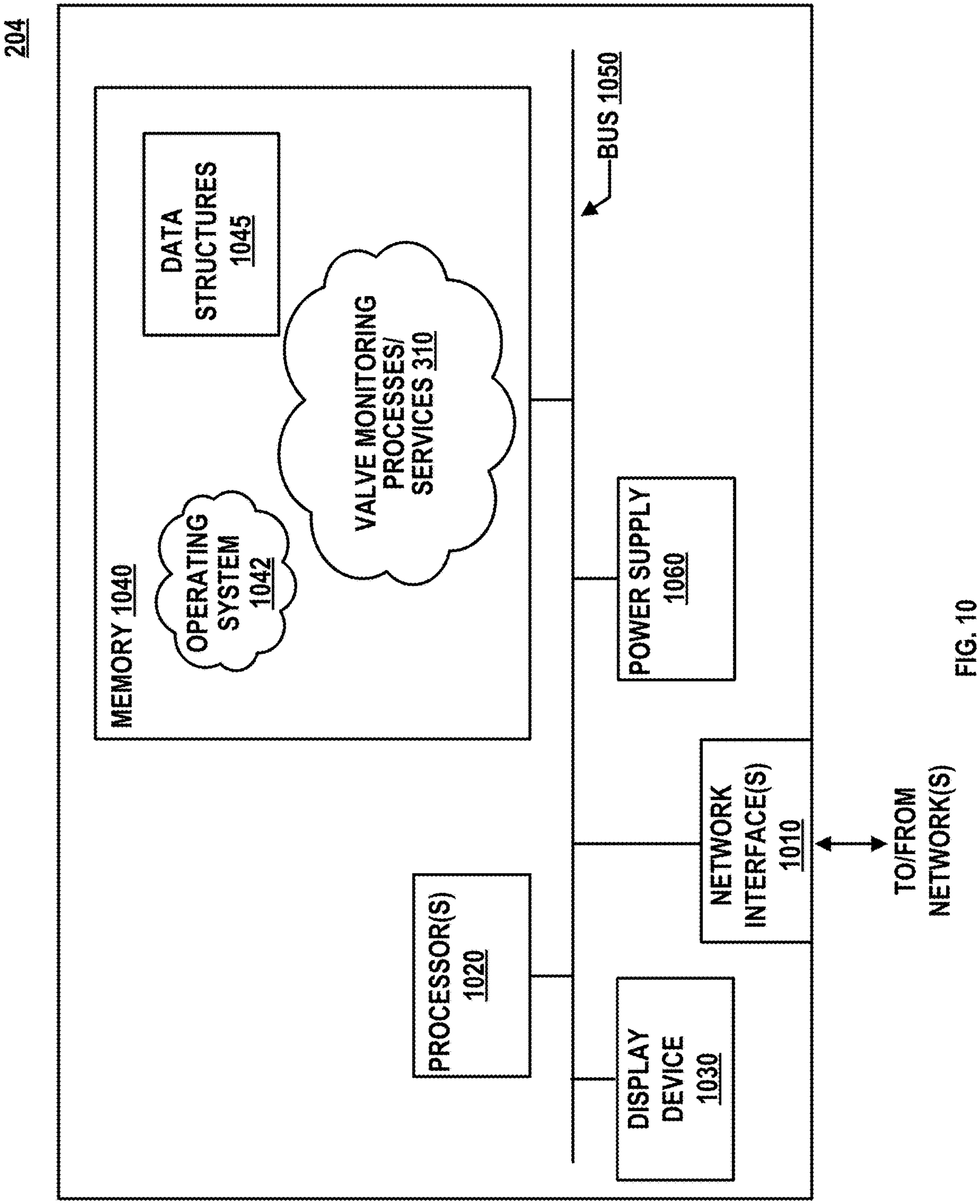
FIG. 10 is a simplified diagram showing an example computing system for implementation of the monitoring system of FIG. 2.

Based on the values of parametric behavior characteristics 332, the behavioral model 320 can infer the operational state 342 of the valve device (e.g., type of failure, or no failure at all), as well as an estimated remaining lifetime 344 of the valve device. These inferences can be made based on how the values of parametric behavior characteristics 332 correlate with known failure states and general lifetime degradation patterns of the valve device. For operational state inference, the behavioral model 320 can apply, for example, a classification technique, The computing device 204 can display information about the indirect operational characteristics 312, the parametric behavior characteristics 332, the operational state 342, and/or the estimated remaining lifetime 344 at a display device (FIG. 10).

4. Indirect Operational Characteristics Example

Figure 2:
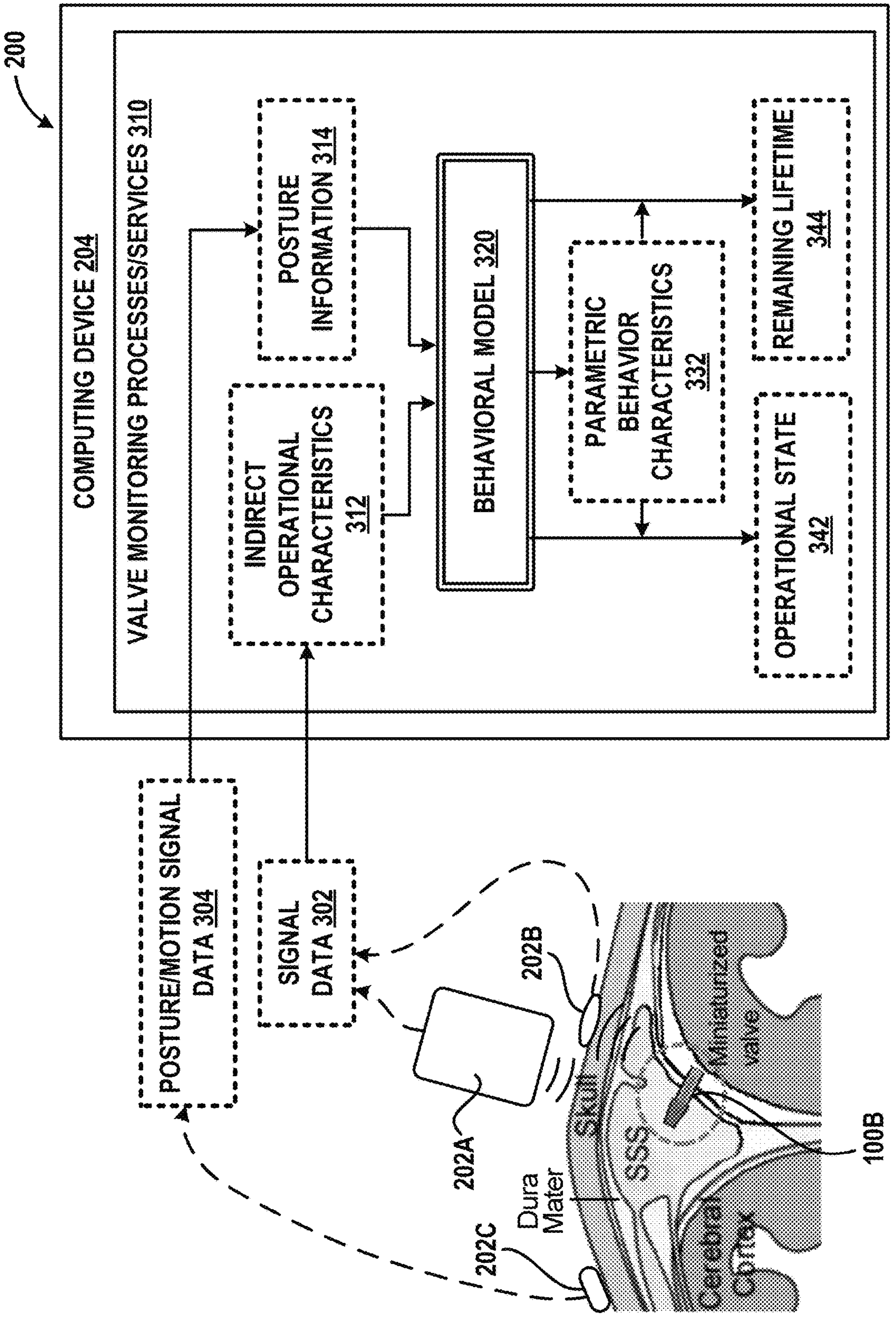
FIG. 2 is a block diagram illustrating a valve monitoring system for monitoring function of a valve system, such as the miniaturized valve system of FIG. 1B.
Figure 3A:
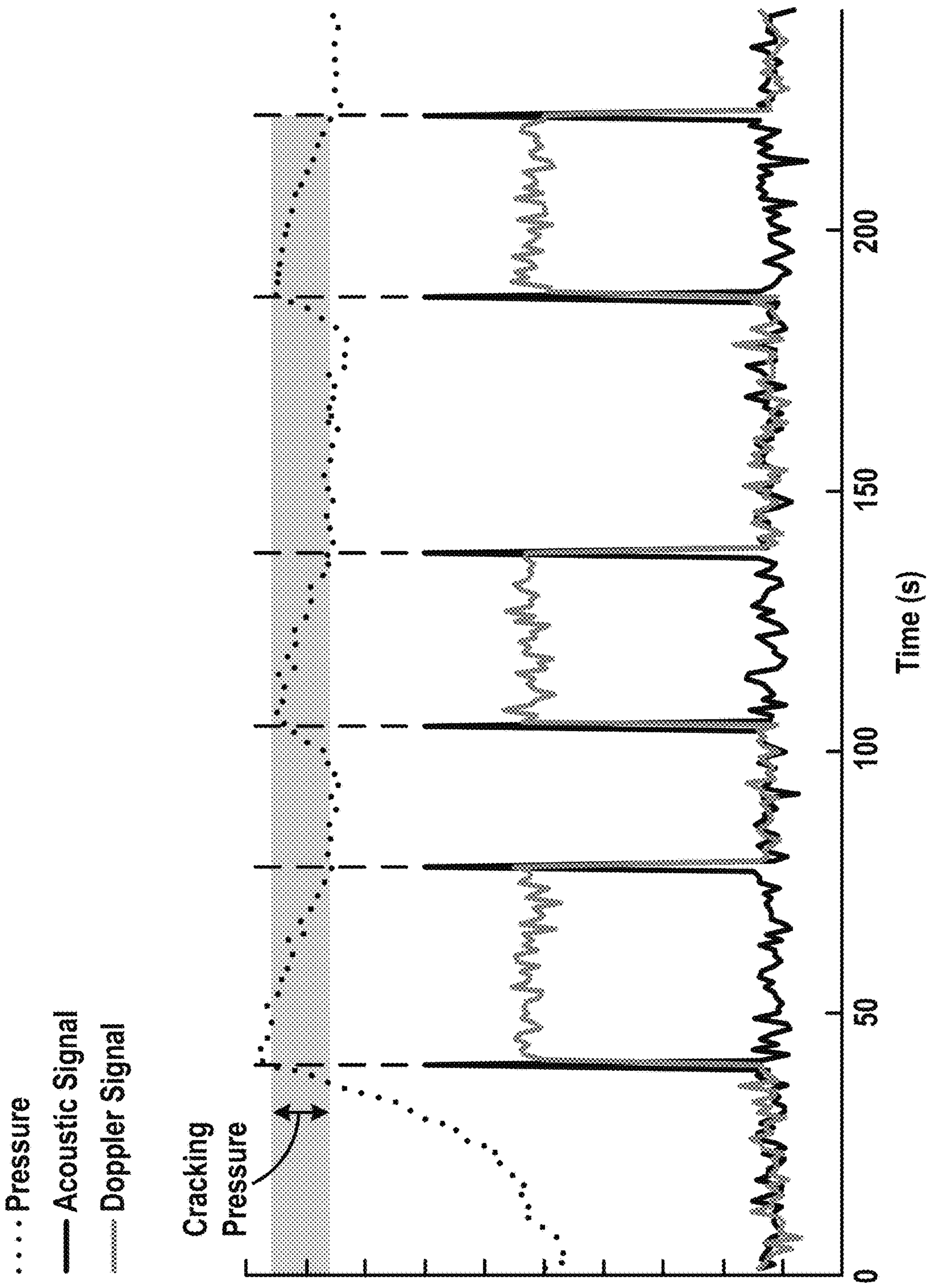
FIG. 3A is a graphical representation showing correlation of an acoustic signal and a Doppler ultrasound signal measurable by the valve monitoring system of FIG. 2 with operational characteristics of a valve system including intracranial pressure and cracking pressure.

FIG. 3A is a graphical representation showing example values of indirect operational characteristics 312 of a valve device measured during in-vivo animal testing over 3 cycles, including an acoustic signal (solid black line) where "spikes" in value correlate with opening or closing actions of the valve device, and further including a Doppler ultrasound signal (solid gray line) where lower values correlate with low to no fluid flow through the valve device and where higher values correlate with fluid flow through the valve device (e.g., during times that the valve device is "open"). Some parametric behavior characteristics 332 are also plotted in FIG. 3A, including ICP (dotted line) and cracking pressure (gray region). As shown, the parametric behavior characteristics 332 correlate with the indirect operational characteristics 312, and with a properly characterized behavioral model (e.g., behavioral model 320 shown in FIG. 2) the parametric behavior characteristics 332 can be inferred based on the indirect operational characteristics 312.

To develop the behavioral model 320, values of various parametric behavior characteristics 332 including ICP, along with the indirect operational characteristics 312 discussed above, can be measured and correlated though various stages of development including equivalent circuit simulation, testbed simulation, and in an animal subject. In particular, the behavioral model 320 can be trained or otherwise developed to examine correlations between the indirect operational characteristics 312 and parametric behavior characteristics 332 so that the indirect operational characteristics 312 may be used by the behavioral model 320 to infer values of parametric behavior characteristics 332 during deployment.

As shown in FIG. 3A, around the time of a first peak in the intracavity pressure (dotted line), a first spike in the acoustic signal (solid black line) can be observed, indicating opening of the valve device. Shortly after the first spike in the acoustic signal, the Doppler ultrasound signal (solid gray line) is also observed changing from a near-zero value to a higher value, indicating fluid flow through the valve device. As the intracavity pressure falls past a certain value, a second spike in the acoustic signal can be observed, indicating closure of the valve device. Shortly after the second spike in the acoustic signal, the Doppler ultrasound signal is also observed changing from the higher value back down to the near-zero value, indicating little to no fluid flow through the valve device. During this time, the intracavity pressure appears to stabilize, until a change in intracavity pressure is induced (e.g., by a posture change, which can be reflected in the posture information 314 referenced in FIG. 2) which causes the valve device to open again and the cycle repeats.

Figure 3B:
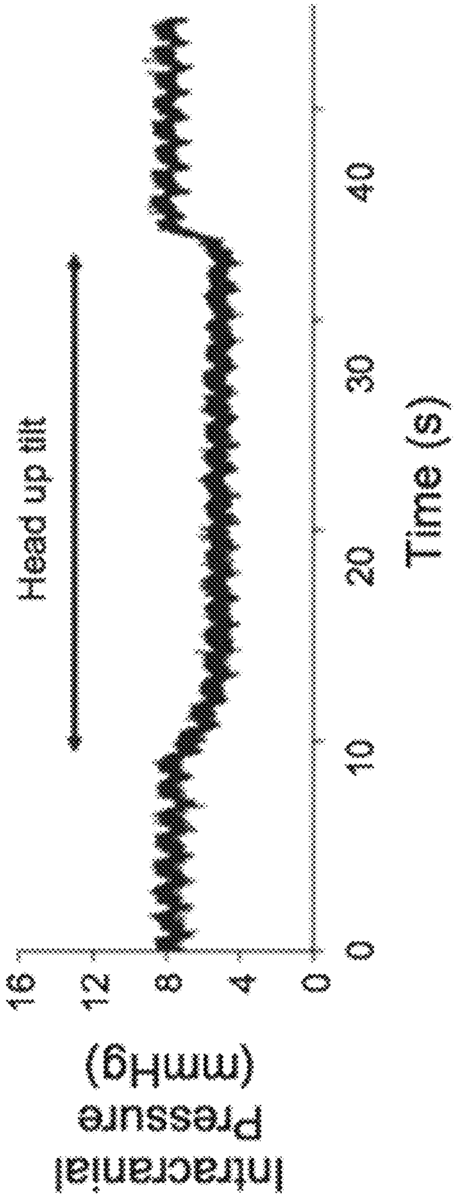
FIGS. 3B and 3C are a pair of graphical representations showing changes in intracranial pressure over posture changes for development and characterization of the valve monitoring system of FIG. 2.
Figure 3C:
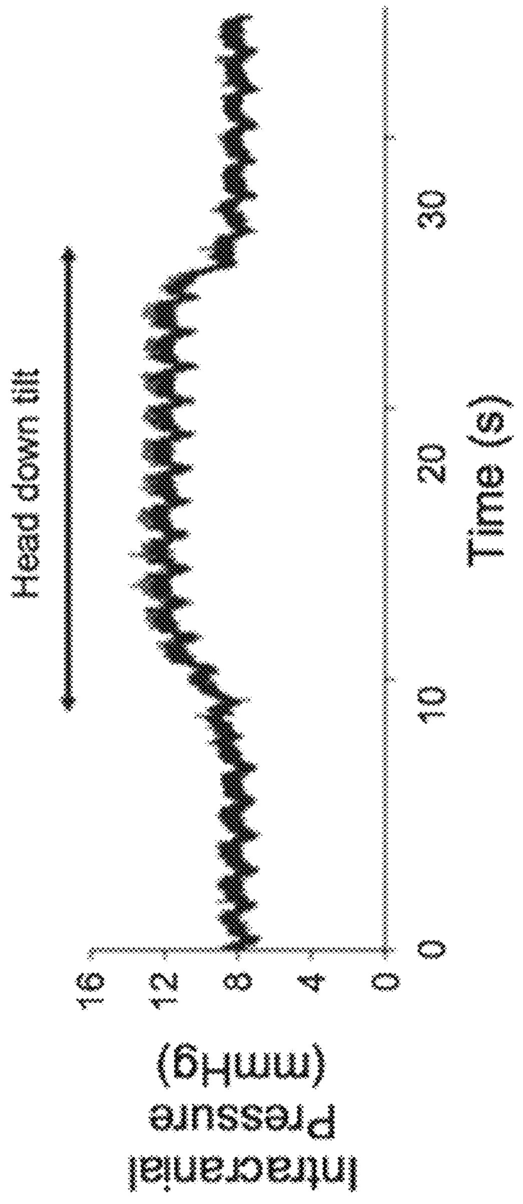

Additionally, referring to FIGS. 3B and 3C, postural changes can affect parametric behavior characteristics 332 such as ICP and should be accounted for by the behavioral model 320. As shown in FIG. 3B, a period in which a user has their head tilted upward corresponds with a clear drop in ICP when compared to a normal or neutral head position. Likewise, as shown in FIG. 3C, a period in which a user has their head tilted downward corresponds with a clear rise in ICP when compared to a normal or neutral head position. As shown in both FIGS. 3B and 3C, the ICP is shown to return to its original range upon return to the normal or neutral head position. As such, the behavioral model 320 can use the posture information 314 referenced in FIG. 2 for context when interpreting the indirect operational characteristics 312.

The value or range of pressure that triggers opening or closure of the valve device can be referred to as the "cracking pressure" of the valve device, which dictates at what value of intracavity pressure the valve device opens or closes to maintain a healthy intracavity pressure. Cracking pressure is an important parameter of the valve device, and a valve device must be designed appropriately to ensure an effective cracking pressure. Even a well-designed valve device may suffer degradation over time that may lead to changes in cracking pressure. As such, cracking pressure is an important value for monitoring valve function. To infer the cracking pressure of an implanted valve, the intracranial pressure may be inferred by examining indirect operational characteristics 312 including timestamps associated with opening and closing actions of the valve device (e.g., by the acoustic signal) and fluid flow through the valve device (e.g., by the Doppler ultrasound signal). This requires development and application of the behavioral model 320 for the valve device in order to correctly infer intracranial pressure based on the indirect operational characteristics 312.

Importantly, the behavioral model 320 should account for design parameters of the valve device (e.g., intended cracking pressures, material properties, dimensions, etc.), fluid mechanics (e.g., established relationships between flow rate, pressure, and resistance in view of the Monro-Kellie doctrine, etc.), surrounding bodily systems (e.g., arrangement and volumes of structures, tissue compliances, and immune responses), and changes in posture (which may be used to induce conditions such as raised intracranial pressure, which can trigger observable responses by the valve device). The behavioral model 320 should also be able to correlate the indirect operational characteristics 312 with a type of failure state (or, a non-failure state) of a valve device. By comparing expected responses of the valve device and bodily system as defined by the behavioral model 320 with observed responses in the form of indirect operational characteristics 312, a functional (operational) state and/or remaining lifetime of the valve device may be inferred.

5. Behavioral Model Development Overview

Figure 4A:
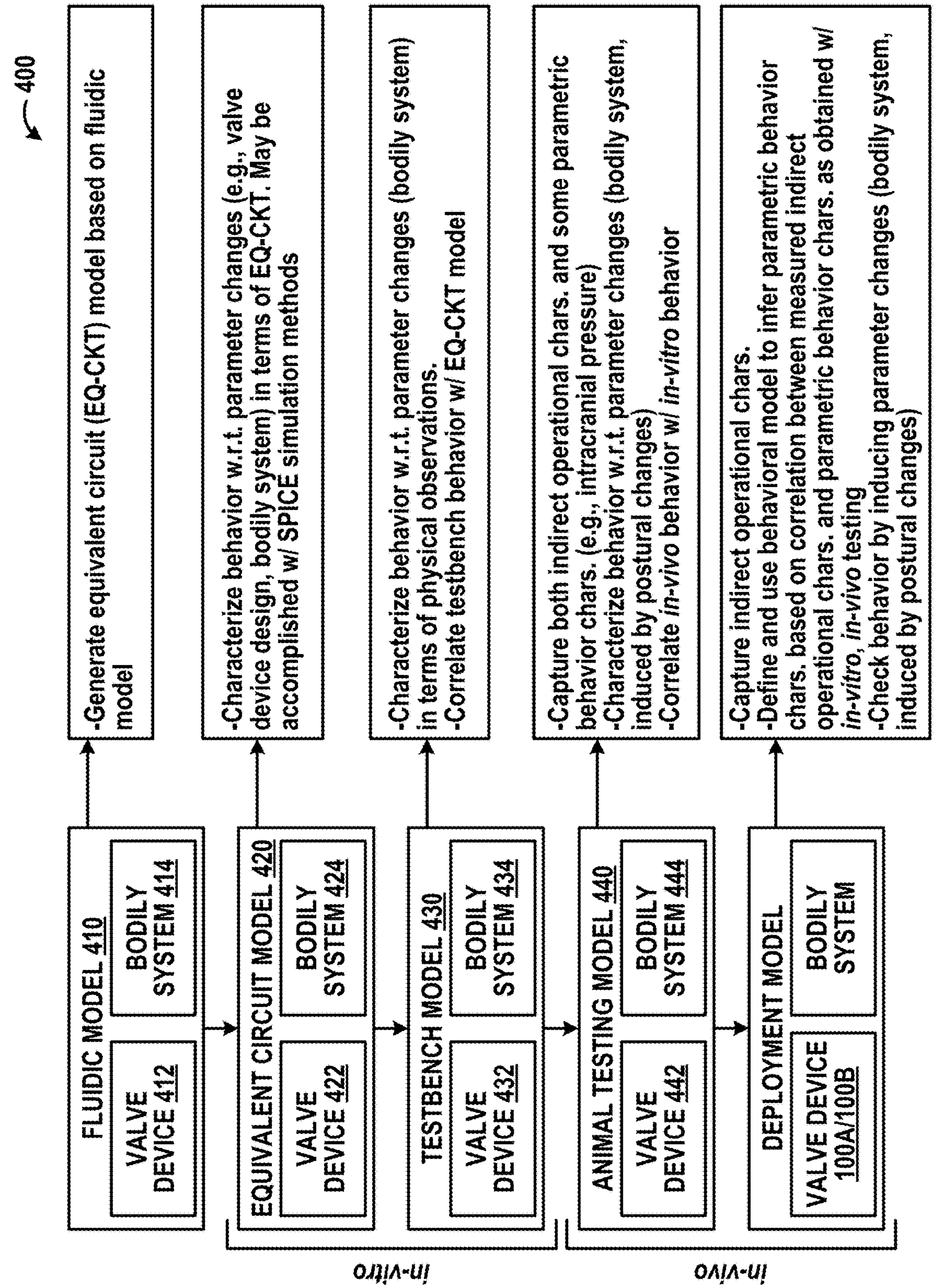
FIGS. 4A and 4B are a pair of diagrams showing development and characterization of a deployment model of the valve monitoring system of FIG. 2 based on a fluidic model, an equivalent circuit model, a testbench model, and an animal testing model of the valve monitoring system of FIG. 2.
Figure 4B:
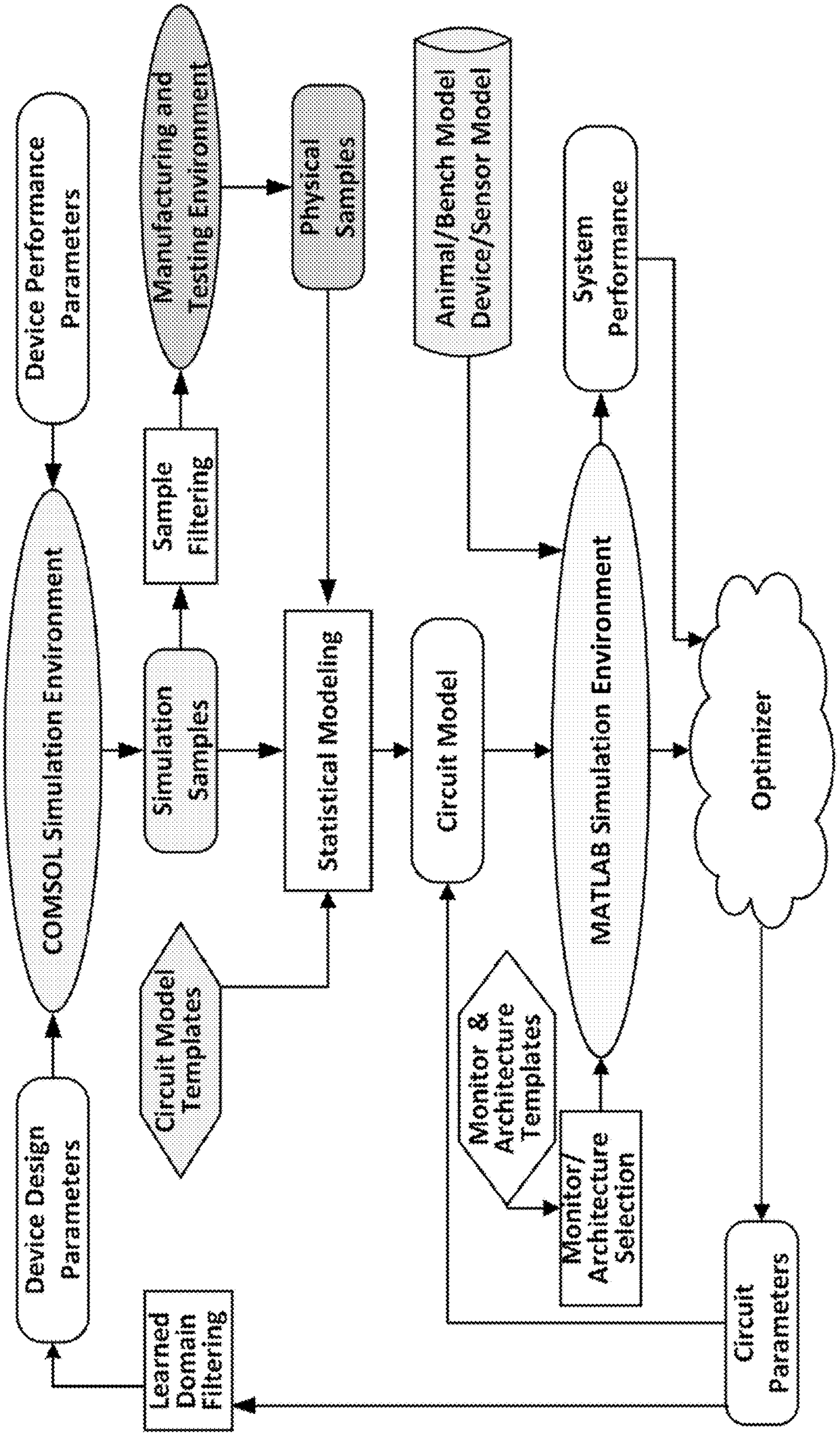

As discussed in a further section herein, development of the behavioral model 320 can be tightly coupled with development and characterization of a valve device. FIG. 4A shows various example stages that are contemplated for development of one embodiment of the behavioral model 320. In the example of FIG. 4A, the behavioral model 320 may be initially developed through in-vitro simulation and testing, (e.g., using an equivalent circuit model and a physical testbench model), and then may be further developed through in-vivo observation (e.g., though animal testing, and allowing for further refinement during deployment). FIG. 4B is a flowchart showing one such process for optimizing valve design and characterization of the behavioral model 320 in terms of collected data and simulation methods.

5.1 In-Vitro Testing

For example, during in-vitro testing, indirect operational characteristics 312 and parametric behavior characteristics 332 can be conceptually correlated with one another. Further, some parametric behavior characteristics 332 such as bodily system parameters can also be simulated and controlled during in-vitro testing to understand correlations between indirect operational characteristics 312 and parametric behavior characteristics 332. Such bodily system parameters can include, for example, intracavity pressure(s), tissue compliances, and fluid resistance(s). In some examples, valve device response to postural changes may be simulated during in-vitro testing by varying one or more bodily system parameters. In-vitro testing can also enable correlation of the indirect operational characteristics 312 and parametric behavior characteristics 332 with design parameters of the valve device (e.g., width, length, diameter, material properties, etc.). In-vitro testing and modeling enables initial development of the behavioral model 320, which correlates relationships between various device and bodily system parameter values, testbed behavior of the valve device, and equivalent circuit behavior of the valve device. In-vitro testing and modeling can also be performed to examine how the lifetime of the valve device changes under various conditions, and to examine how the behavior of the valve device can indicate remaining lifetime of the valve device. During in-vitro testing, aspects of the valve device and behavioral model 320 that corresponds with the valve device may be continually refined. In some embodiments, in-vitro testing can include development and simulation of "equivalent circuit" models followed by physical implementation and simulation of "testbed" models, avoiding iterative design and simulation methods that would be computationally or procedurally expensive and/or infeasible.

As shown in diagram 400 of FIG. 4A, in-vitro testing for development of a valve device and/or a behavioral model 320 for the valve device can start with a fluidic model 410 of a valve device 412 and its interaction with a bodily system 414. Based on the fluidic model 410, indirect operational characteristics 312 and parametric behavior characteristics 332 as well as bodily system parameters can be conceptually correlated with one another.

5.2 In-Vitro Testing: Equivalent Circuit Model

Figure 5A:
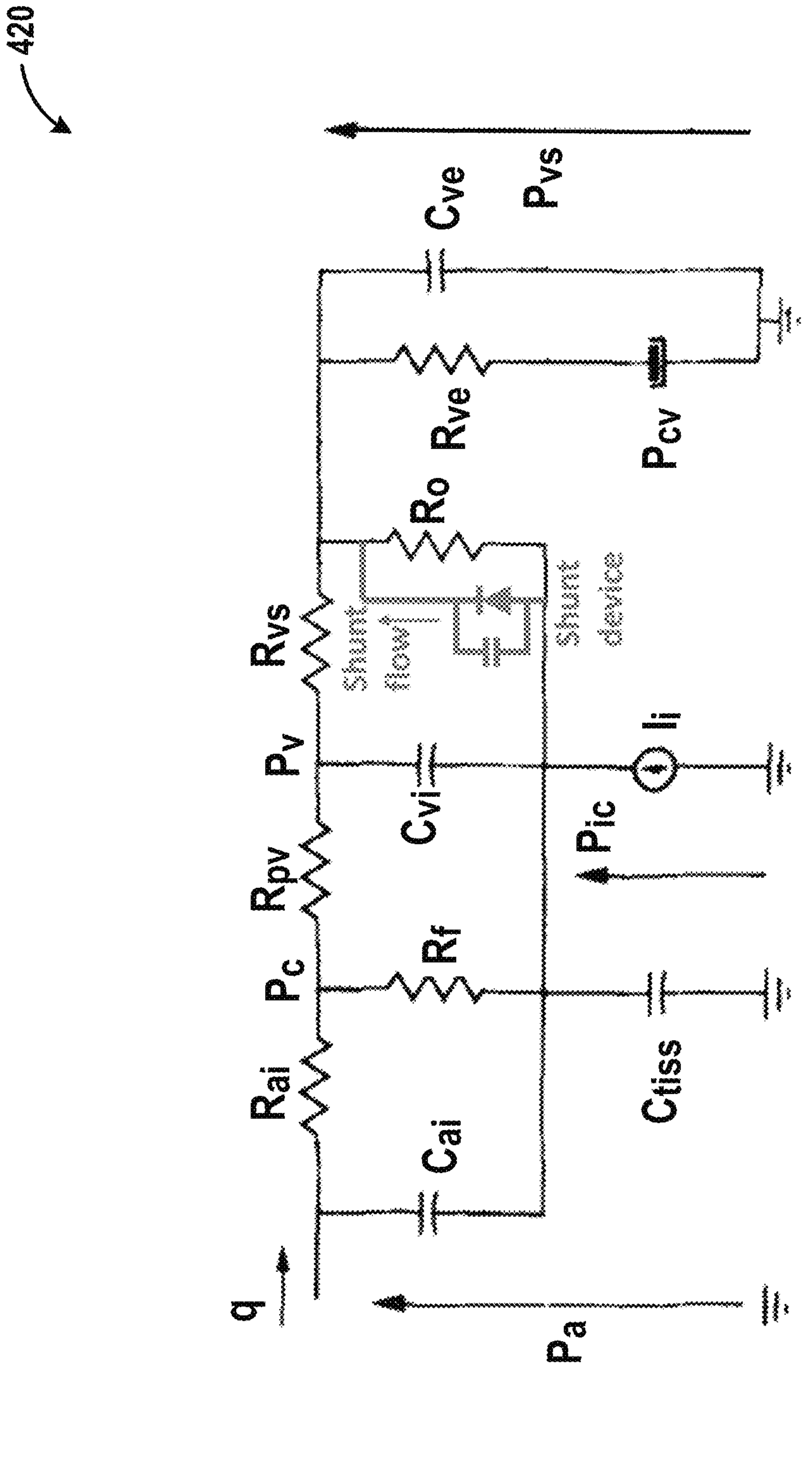
FIG. 5A is a schematic diagram showing an example of the equivalent circuit model of FIG. 4A for development and characterization of the valve monitoring system of FIG. 2.
Figure 5B:
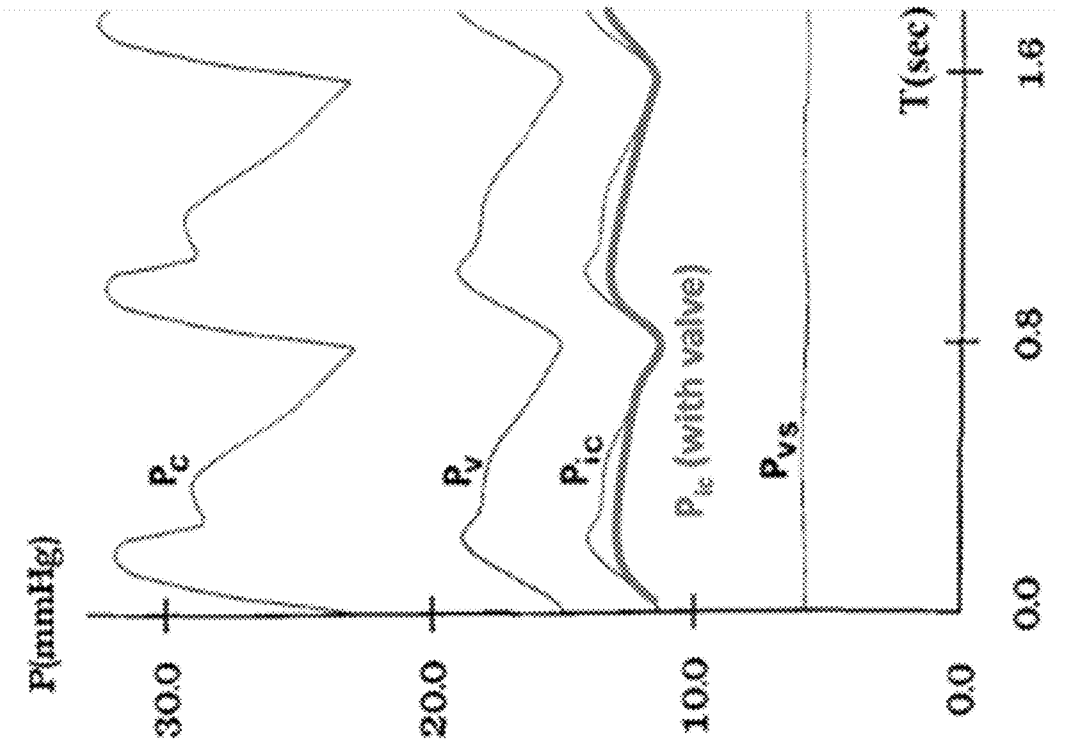
FIG. 5B is a graphical representation showing various operational characteristics of the valve monitoring system of FIG. 2 as simulated using the equivalent circuit model of FIG. 5A.

The fluidic model 410 can be conceptual in nature, and can be used to generate an equivalent circuit model 420 of a valve device 422 and its interaction with a bodily system 424 based on the fluidic model 410. The equivalent circuit model 420 allows simulation and monitoring with conventional circuit simulation and analysis methods. Using the equivalent circuit model 420, initial characterization of the behavioral model 320 can take place with respect to parameter changes in terms of an equivalent circuit. Valve design choices may also be refined using the equivalent circuit model 420 to optimize aspects of the valve design and/or its interaction with the bodily system. Such an example is shown in FIGS. 5A and 5B, where FIG. 5A shows the equivalent circuit model 420 and FIG. 5B plots various pressure values (analogous to voltage) of the equivalent circuit model 420 relative to one another over time. Various design choices and their consequences may be observed using the equivalent circuit model 420 to reduce unnecessary resource consumption associated with repeated fabrication and implementation of physical models.

5.3 In-Vitro Testing: Testbench Model

With further reference to FIGS. 4A and 4B, a testbench model 430 of a valve device 432 and a bodily system 434 can be developed based on the equivalent circuit model 420. The valve device 432 of the testbench model 430 can be physically fabricated based on design parameters that were optimized using the equivalent circuit model 420. The testbench model 430 allows simulation and monitoring with physical fluids that mimic the bodily system of a user (or an animal). Using the testbench model 430, further characterization of the behavioral model 320 can take place with respect to physical implementation of the valve device in a controlled environment. Valve design choices may also be refined using the testbench model 430 to optimize aspects of the valve design and/or its interaction with the bodily system, as well as account for potential failure points and problems that the equivalent circuit model 420 was not able to account for. The behavior of the valve device 432 and the bodily system 434 of the testbench model 430 can be correlated with that of the valve device 422 and the bodily system 424 of the equivalent circuit model 420.

Figure 6:
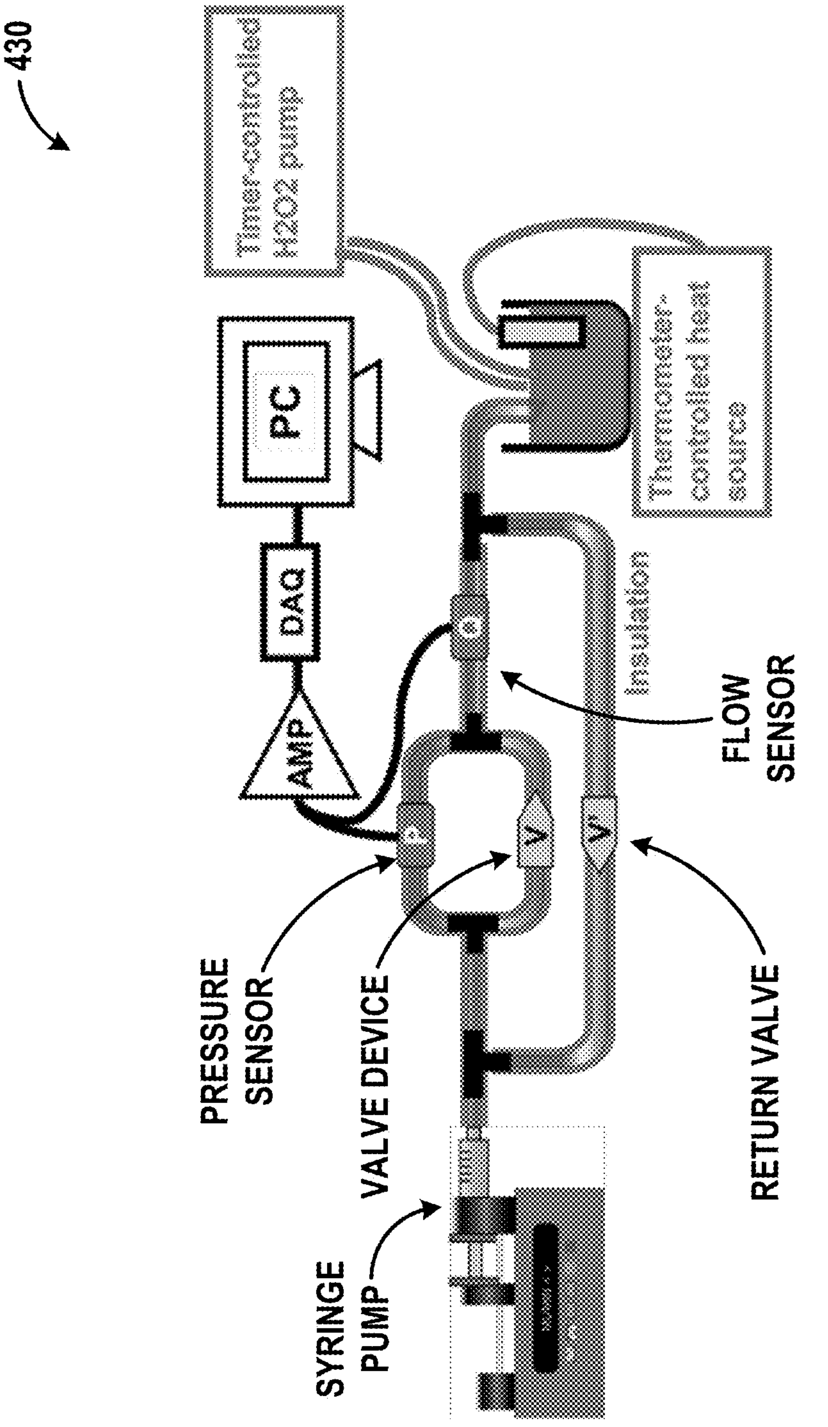
FIG. 6 is a simplified diagram showing an example of the testbench model of FIG. 4A for development and characterization of the valve monitoring system of FIG. 2.

FIG. 6 shows an example of the testbench model 430 that can be physically implemented and simulated, and correlates with the equivalent circuit model of FIGS. 5A and 5B. Aspects of the bodily system 434 can be physically simulated and controlled using various devices including a syringe pump, sensors including those that measure indirect operational characteristics 312 (acoustic and ultrasound sensors) and parametric behavior characteristics 332 (pressure and flow sensors), and a heat source (e.g., to mimic bodily temperatures as well as changes in bodily temperatures). In particular, values associated with the bodily system 434 (e.g., flow rate, intracavity pressure, etc.) may be measured and controlled using the testbench model 430 to observe how the valve device 432 behaves under various conditions (including normal conditions and accelerated aging conditions). The testbench model 430 may be used to develop some aspects of the behavioral model 320 including indicators of how the valve device may degrade over time or under certain conditions. Mechanical failure states of the valve device and its effect on the bodily system may also be observed using the testbench model 430. Observations collected using the testbench model 430 may be correlated with observations collected using the equivalent circuit model 420 for development of the behavioral model 320.

5.4 In-Vivo (Animal) Testing

As further indicated in FIGS. 4A and 4B, after successful implementation of the testbench model 430, in-vivo testing can further develop the behavioral model 320 as well as refine the valve device. During in-vivo animal testing using an animal testing model 440 of a valve device 442 and its interaction with a bodily system 444, some parametric behavior characteristics 332 such as ICP may be directly measured using pressure sensors, along with the indirect operational characteristics 312 that would be measured during deployment within a human. Example measurements that may be captured during in-vivo animal testing are shown in FIGS. 3A-3C discussed above. For further development of the behavioral model 320, measured values and observations made during in-vivo animal testing can be correlated with patterns and values found during in-vitro testing and modeling, e.g., through observations collected using the equivalent circuit model 420 and the testbench model 430. The behavioral model 320 may be further developed by correlating the indirect operational characteristics 312 with (directly-measured) parametric behavior characteristics 332 in view of factors that are not easily accounted for during in-vitro testing, such as post-surgical inflammation and foreign body response. The behavioral model 320 can also be refined in view of postural changes of an animal, which can induce variations in bodily system parameters that may be correlated with those observed during in-vitro testing.

Figure 7A:
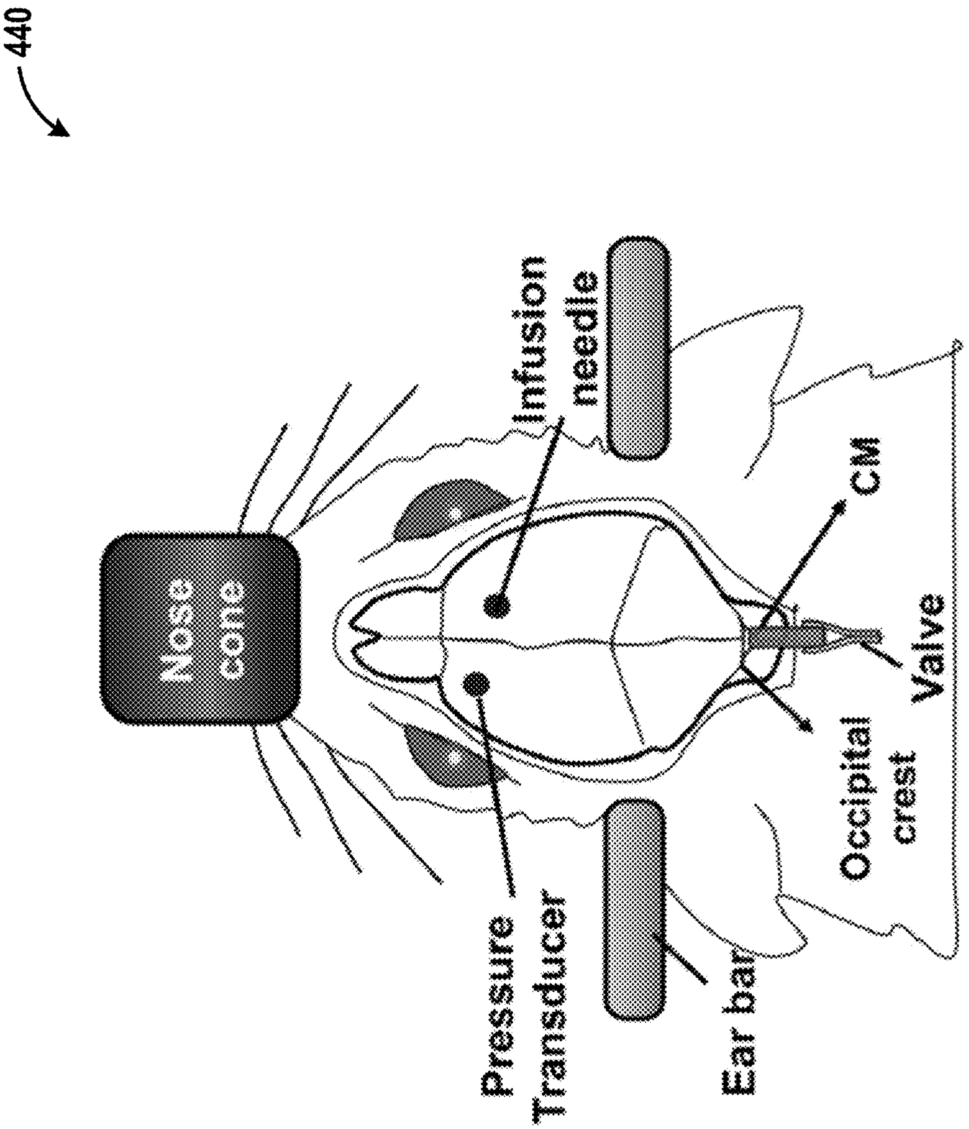
FIG. 7A is a simplified illustration showing an example of the animal testing model of FIG. 4A from an above cross-sectional perspective for development and characterization of the valve monitoring system of FIG. 2.
Figure 7B:
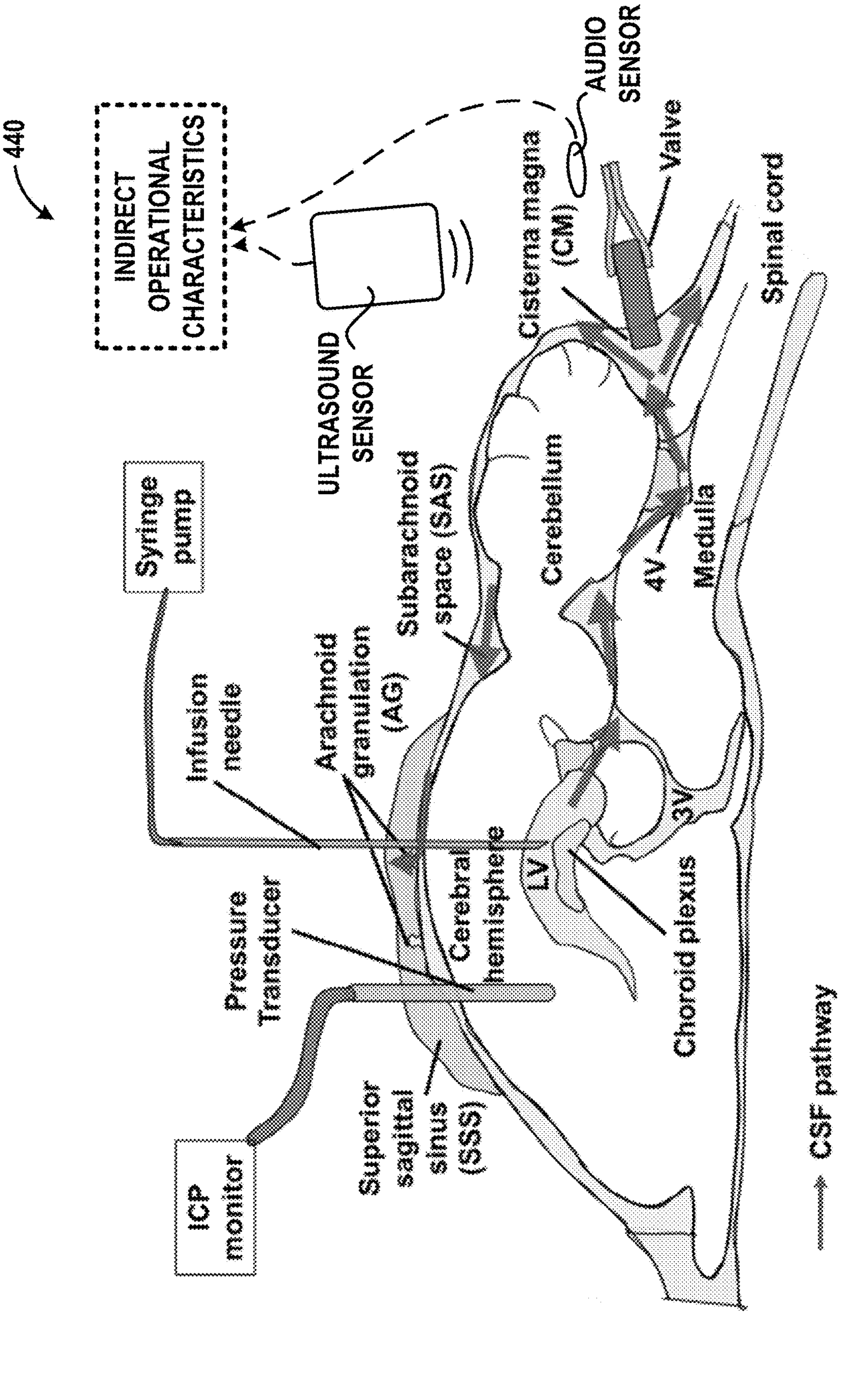
FIG. 7B is a simplified illustration showing an example of the animal testing model of FIG. 7A from a side cross-sectional perspective for development and characterization of the valve monitoring system of FIG. 2.

FIGS. 7A and 7B show an example of the animal testing model 440 of the valve device 442 and its interaction with the bodily system 444, discussed in greater detail in section 8.5.4.

Further, while the examples discussed herein outline a rodent model for animal testing, the animal testing model 440 could be carried out using any suitable animal model. For example, “animal” can encompass vertebrates such as mammals (e.g., primates, mice, dogs, cats, rabbits), or non-mammal vertebrates such as but not limited to fish, or birds. In some examples, “primates” can encompass humans and non-human primates such as but not limited to chimpanzees, monkeys, and lemurs.

5.5 In-Vivo Deployment Model

Finally, with continued reference to FIGS. 4A and 4B, a deployment model of the monitoring system 200, including the valve device (e.g., valve device 100A or 100B) and the bodily system (e.g., of the user) can be implemented for end-users as shown in FIG. 2. The process illustrated in FIGS. 4A and 4B enables development of the behavioral model 320 which correlates measured indirect operational characteristics 312 with values of parametric behavior characteristics 332, including measured values found during in-vitro and in-vivo simulation and testing. As such, upon human deployment of the valve device monitoring system 200 in association with the valve device as shown in FIG. 2, the behavioral model 320 enables inference of values of parametric behavior characteristics 332 based on measured values of indirect operational characteristics 312 in view of animal testing, testbench simulations, and equivalent circuit simulations of the valve device within a (modeled) bodily system. The behavioral model 320 enables monitoring of the valve device using non-invasive sensing modalities (e.g., microphones, ultrasound) by correlating the indirect operational characteristics 312 with other parameters (parametric behavior characteristics 332) that are difficult to monitor in real-time. During use, the computing device 204 of the monitoring system 200 may prompt the user to perform posture changes that induce bodily system parameter changes, which in turn can induce behaviors from the valve device to be monitored by the monitoring system 200. The behavioral model 320 can also be used to improve understanding of valve system design by modeling behavioral consequences of design changes and overall system changes. Further, the behavioral model 320 may be refined in view of real data obtained from real-life deployment.

6. Methods

Figure 8:
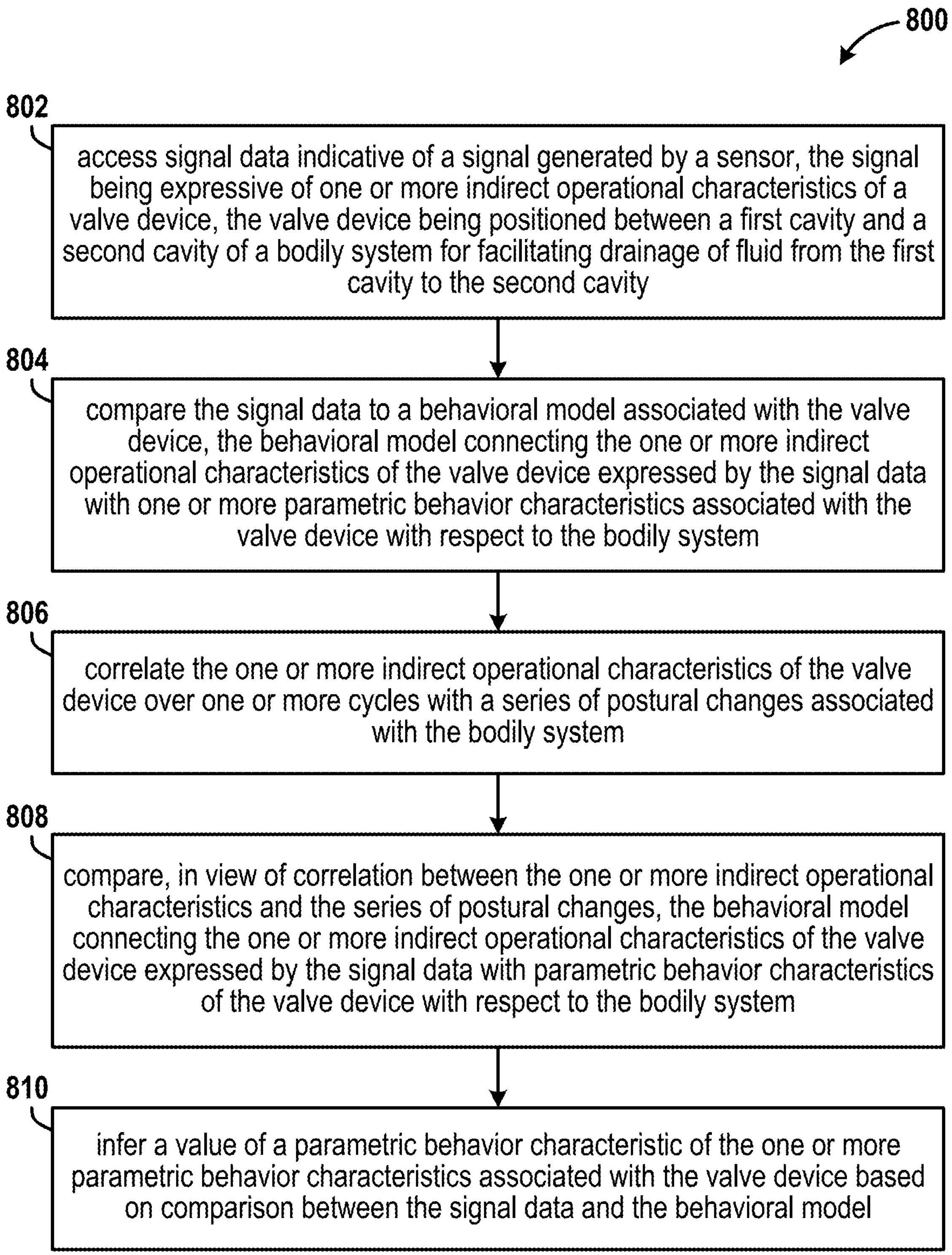
FIG. 8 is a process flow diagram showing a first method of inferring a value of a parametric behavior characteristic that indicates function of a valve device using a behavioral model of the valve device by the valve monitoring system of FIG. 2.

FIG. 8 shows a first method 800 of inferring a value of a parametric behavior characteristic that indicates function of a valve device using a behavioral model of the valve device. Instructions corresponding with steps of first method 800 can be stored or otherwise accessible by the computing device 204 for implementation of aspects of monitoring system 200.

Step 802 of first method 800 includes accessing signal data indicative of a signal generated by a sensor, the signal being expressive of one or more indirect operational characteristics of a valve device, the valve device being positioned between a first cavity and a second cavity of a bodily system for facilitating drainage of fluid from the first cavity to the second cavity. The one or more indirect operational characteristics of the valve device can include one or more of: an opening time of the valve device associated with an opening action of the valve device over one or more cycles; a closing time of the valve device associated with a closing action of the valve device over the one or more cycles; and a flow rate of fluid through the valve device over the one or more cycles.

Step 804 of first method 800 includes comparing the signal data to a behavioral model associated with the valve device, the behavioral model connecting the one or more indirect operational characteristics of the valve device expressed by the signal data with one or more parametric behavior characteristics associated with the valve device with respect to the bodily system. The one or more parametric behavior characteristics of the valve device can include one or more of: an intracavity pressure associated with the first cavity over one or more cycles; a cracking pressure of the valve device; and a reverse flow rate associated with backflow of fluid from the second cavity to the first cavity over the one or more cycles.

Step 806 of first method 800 includes correlating the one or more indirect operational characteristics of the valve device over one or more cycles with a series of postural changes associated with the bodily system. Step 808 of first method 800 includes comparing, in view of correlation between the one or more indirect operational characteristics and the series of postural changes, the behavioral model connecting the one or more indirect operational characteristics of the valve device expressed by the signal data with parametric behavior characteristics of the valve device with respect to the bodily system. Step 810 of first method 800 includes inferring a value of a parametric behavior characteristic of the one or more parametric behavior characteristics associated with the valve device based on comparison between the signal data and the behavioral model.

Figure 9A:
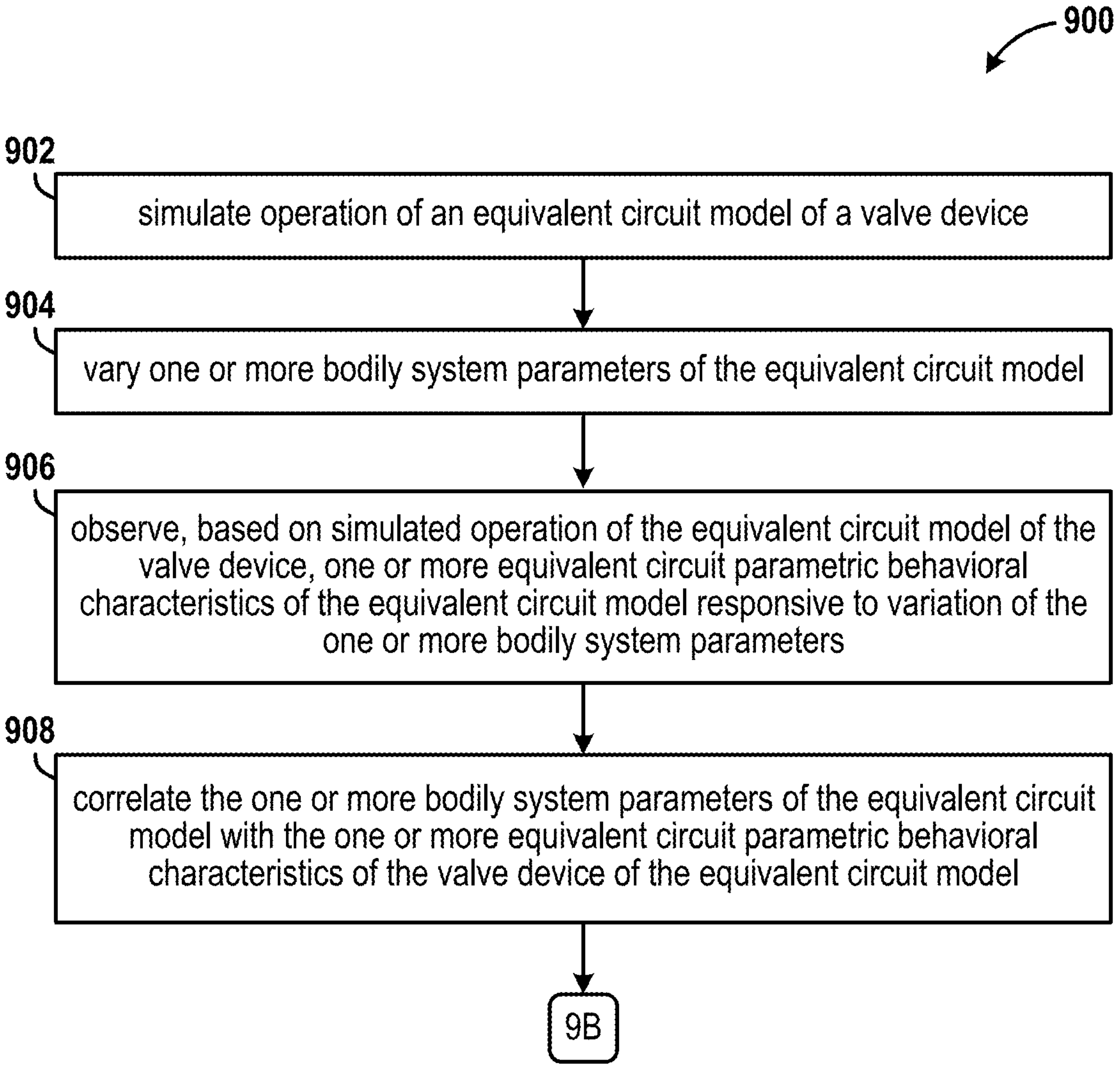
FIGS. 9A and 9B are a pair of process flow diagrams showing a second method of developing the behavioral model of FIG. 2 for use in inferring a value of a parametric behavior characteristic that indicates function of a valve device.
Figure 9B:
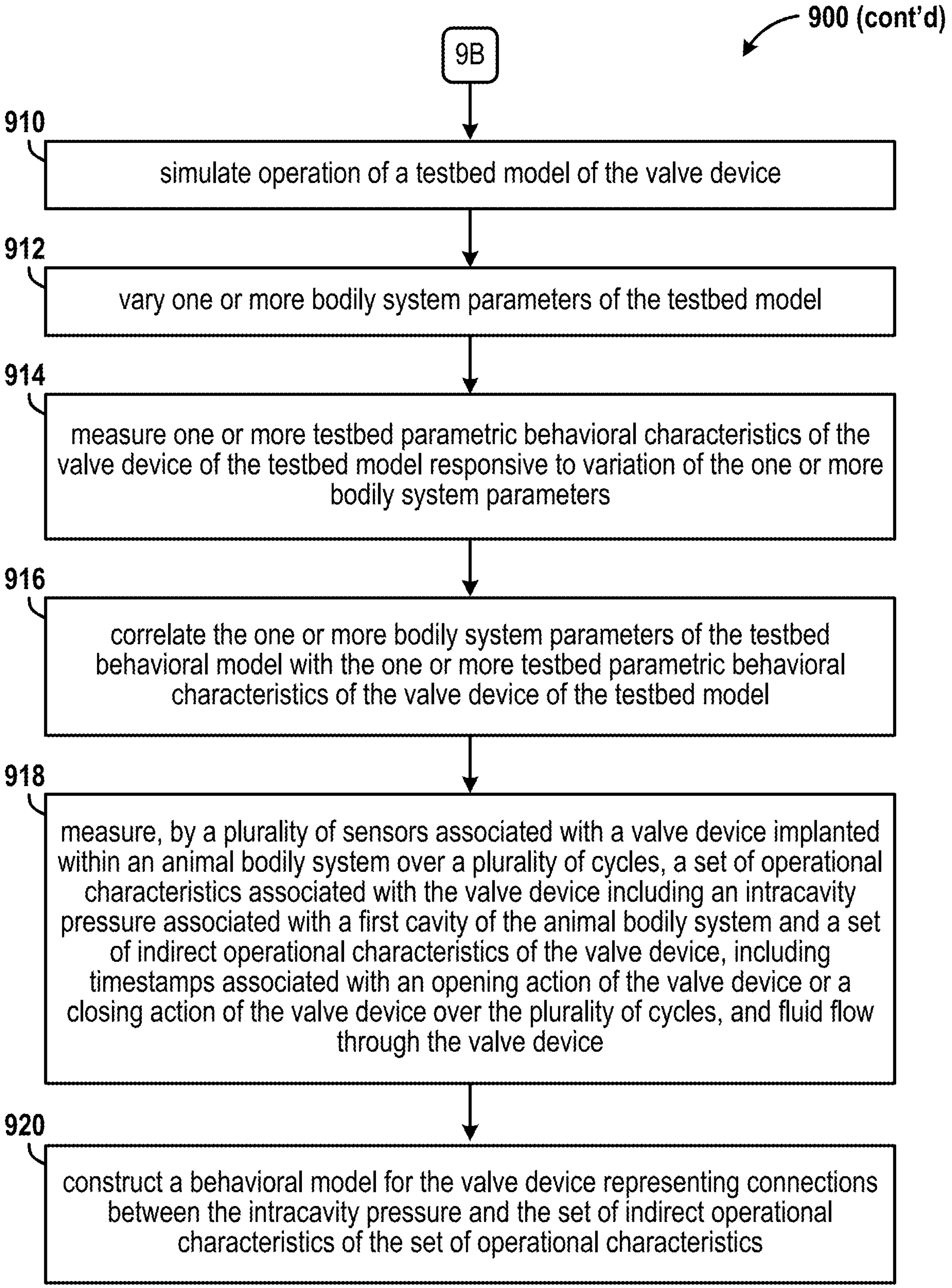

FIGS. 9A and 9B illustrate a second method 900 of developing a behavioral model for use in inferring a value of a parametric behavior characteristic that indicates function of a valve device. The second method 900 can be implemented at a computing device that may be the same or similar structure as computing device 204 discussed in further detail at FIG. 10. The second method 900 may also be implemented in a distributed manner, e.g., using more than one computing device. The second method 900 correlates with development of the behavioral model 320 of the monitoring system 200 (FIG. 2) as in FIGS. 4A-7B.

As shown in FIG. 9A, step 902 of second method 900 includes simulating operation of an equivalent circuit model of a valve device. Step 904 of second method 900 includes varying one or more bodily system parameters of the equivalent circuit model. Step 906 of second method 900 includes observing, based on simulated operation of the equivalent circuit model of the valve device, one or more equivalent circuit parametric behavioral characteristics of the equivalent circuit model responsive to variation of the one or more bodily system parameters. Step 908 of second method 900 includes correlating the one or more bodily system parameters of the equivalent circuit model with the one or more equivalent circuit parametric behavioral characteristics of the valve device of the equivalent circuit model. FIG. 9A ends at (9B), and method 900 continues at (9B) of FIG. 9B.

Referring to FIG. 9B, step 910 of second method 900 includes simulating operation of a testbed model of the valve device. Step 912 of second method 900 includes varying one or more bodily system parameters of the testbed model. Step 914 of second method 900 includes measuring one or more testbed parametric behavioral characteristics of the valve device of the testbed model responsive to variation of the one or more bodily system parameters. Step 916 of second method 900 includes correlating, for the testbed behavioral model, of the one or more bodily system parameters with the one or more testbed parametric behavioral characteristics of the valve device of the testbed model.

Step 918 of second method 900 includes measuring, by a plurality of sensors associated with a valve device implanted within an animal bodily system over a plurality of cycles, a set of operational characteristics associated with the valve device including an intracavity pressure associated with a first cavity of the animal bodily system and a set of indirect operational characteristics of the valve device, including timestamps associated with an opening action of the valve device or a closing action of the valve device over the plurality of cycles, and fluid flow through the valve device. Step 920 of second method 900 includes constructing a behavioral model for the valve device representing connections between the intracavity pressure and the set of indirect operational characteristics of the set of operational characteristics.

The behavioral model constructed at step 920 expresses a correlation between the set of operational characteristics and a series of postural changes exhibited by the animal bodily system. Further, the behavioral model incorporates an equivalent circuit behavioral model in terms of an equivalent circuit model of the valve device and the animal bodily system, the equivalent circuit behavioral model representing connections between one or more design parameters of the valve device, one or more bodily system parameters including intracavity pressure, and one or more equivalent circuit parametric behavioral characteristics of the valve device. The behavioral model also incorporates connections between the equivalent circuit behavioral model and the set of operational characteristics associated with the valve device and the animal bodily system.

In a further aspect, the behavioral model incorporates a testbed behavioral model in terms of a testbed model of the valve device and the animal bodily system, the testbed behavioral model representing connections between one or more design parameters of the valve device, one or more bodily system parameters including intracavity pressure, and one or more testbed parametric behavioral characteristics of the valve device based on the testbed model. Likewise, the behavioral model incorporates connections between the testbed behavioral model and the set of operational characteristics associated with the valve device and the animal bodily system, as well as connections between the testbed behavioral model and an equivalent circuit behavioral models.

The functions performed in the processes and methods may be implemented in differing order. Furthermore, the outlined steps and operations are provided as examples, and some of the steps and operations may be optional, combined into fewer steps and operations, or expanded into additional steps and operations without detracting from the essence of the disclosed embodiments.

7. Computing System

FIG. 10 is a schematic block diagram showing an example configuration of computing device 204 that may be used with one or more embodiments described herein, e.g., as a component of monitoring system 200 and/or as computing device 204 shown in FIG. 2.

Device 204 comprises one or more network interfaces 1010 (e.g., wired, wireless, PLC, etc.), at least one processor 1020, and a memory 1040 interconnected by a system bus 1050, as well as a power supply 1060 (e.g., battery, plug-in, etc.). Device 204 can also include a display device 1030 that can display prompts to a user for initiating posture changes, as well as display results that indicate aspects of valve device functionality including, but not limited to, values of indirect operational characteristics 312, parametric behavior characteristics 332, an operational state 342 of the valve device, and/or a remaining lifetime 344 of the valve device.

Network interface(s) 1010 include the mechanical, electrical, and signaling circuitry for communicating data over the communication links coupled to a communication network, including interfaces with the one or more sensors (e.g., ultrasound sensor 202A, acoustic sensor 202B, and/or posture sensor 202C). Network interfaces 1010 are configured to transmit and/or receive data using a variety of different communication protocols. As illustrated, the box representing network interfaces 1010 is shown for simplicity, and it is appreciated that such interfaces may represent different types of network connections such as wireless and wired (physical) connections. Network interfaces 1010 are shown separately from power supply 1060, however it is appreciated that the interfaces that support PLC protocols may communicate through power supply 1060 and/or may be an integral component coupled to power supply 1060.

Memory 1040 includes a plurality of storage locations that are addressable by processor 1020 and network interfaces 1010 for storing software programs and data structures associated with the embodiments described herein. In some embodiments, device 204 may have limited memory or no memory (e.g., no memory for storage other than for programs/processes operating on the device and associated caches). Memory 1040 can include instructions executable by the processor 1020 that, when executed by the processor 1020, cause the processor 1020 to implement aspects of the monitoring system 200 and the methods 800 or 900 outlined herein.

Processor 1020 comprises hardware elements or logic adapted to execute the software programs (e.g., instructions) and manipulate data structures 1045. An operating system 1042, portions of which are typically resident in memory 1040 and executed by the processor, functionally organizes device 204 by, inter alia, invoking operations in support of software processes and/or services executing on the device. These software processes and/or services may include Valve Monitoring processes/services 310, which can include aspects of first method 800, second method 900, and/or implementations of various modules described herein. Note that while Valve Monitoring processes/services 310 is illustrated in centralized memory 1040, alternative embodiments provide for the process to be operated within the network interfaces 1010, such as a component of a MAC layer, and/or as part of a distributed computing network environment.

It will be apparent to those skilled in the art that other processor and memory types, including various computer-readable media, may be used to store and execute program instructions pertaining to the techniques described herein. Also, while the description illustrates various processes, it is expressly contemplated that various processes may be embodied as modules or engines configured to operate in accordance with the techniques herein (e.g., according to the functionality of a similar process). In this context, the term module and engine may be interchangeable. In general, the term module or engine refers to model or an organization of interrelated software components/functions. Further, while the Valve Monitoring processes/services 310 is shown as a standalone process, those skilled in the art will appreciate that this process may be executed as a routine or module within other processes.

8. Expanding Electronic Design Automation to Biomechanical Medical Devices Through In-Vitro Models The present disclosure investigates wireless, passive, in-situ monitoring of valve devices by the individuals, enabling them to perform self-monitoring akin to diabetic glucose self-monitoring. This will empower the individual to better understand their health status and seek preemptive care rather than responsive care when symptoms arise. This is especially impactful for diseases such as hydrocephalus where symptoms may go undiagnosed until valve failure has already occurred. In addition, gathering data over time to monitor the functionality of the valve provides valuable insights into how failures occur. This data can be used to create machine learning (ML) algorithms to better inform the design and predict failure and remaining lifetime. For example, ML algorithms can be used to search for an optimum between using a single low-failure valve vs. using multiple valves to build a failure-resilient system.

To enable this human-in-the-loop system, multiple approaches are outlined for monitoring the valve devices, including Doppler ultrasound and acoustic sensing as outlined above with respect to FIGS. 2-3C. Using non-invasive sensing modalities enables a simpler, more robust battery-free implant with complexity kept exterior to the body, thereby minimizing risk to the individual. As an individual moves through a sequence of positions, the monitoring system 200 of FIG. 2 can monitor changes in the behavior of the valve device that can be correlated with a well-characterized behavioral model of the valve device to determine or otherwise quantify degradation of valve device functionality over time.

The present disclosure provides a generalized approach to leverage the tools of design automation for novel medical devices. As the framework is built, the generalized approach can be extended to a broader set of devices beyond implantable valves.

8.1 Development of Monitoring Systems

Bio-Electro-Mechanical Modeling Approach: In some embodiments, the fluidic model 410 as shown in FIG. 4A is created for an implanted system including the valve device 412 and surrounding anatomy (bodily system 414). In such embodiments, the fluidic model 410 can be translated into the equivalent circuit model 420 that will enable usage of classic circuit modeling techniques and tools. Highly optimized circuit-specific tools such as Monte Carlo simulations can be used to investigate variations in both the anatomical and engineered components of the system. This enables exploration of a highly-dimensional, wide dynamic range design space. To validate the results from the equivalent circuit model 420, finite element analysis can be used to investigate complex multi-physics in the system. Finite element modeling (FEM) is inherently more computationally intense, thus the design space is reduced via circuit design tools prior to validation with finite element modeling. With progression through the other aims, empirical results will inform the refinement of the models in an iterative manner.

Test bed for long-term fluidic in vitro studies: In some embodiments, completed simulation studies will inform the fabrication of devices for evaluation in the test bed, e.g., through the testbench model 430 of FIG. 4A. Empirical testing approaches further narrow the design space and validate simulation results from the equivalent circuit model 420. In some embodiments, these studies can be approached in a benchtop fluidic test bed to implement long-term studies that enables placement of fabricated devices into a system that can repeatedly actuate the valve devices to determine life-time and failure mechanisms.

In vivo studies with in situ monitoring: In some embodiments, valve devices can be tested in a rodent model to determine the performance and characterize behavioral models of the valve devices relative to the benchtop and simulation models. In such embodiments, this may allow further refinement of the valve devices as well as the behavioral models. In some embodiments, in-vivo study enables the use of in situ monitoring of the valve devices using minimally-invasive modalities, including both Doppler ultrasound and acoustic sensing. In some embodiments, behavioral models can be refined based on the data from the in situ sensing, performance of the valve devices can be mapped to the corresponding simulation and benchtop models. In some embodiments, in-vivo study also enables examination of complex responses not present in either the simulation or benchtop models such as inflammation due to surgical trauma, foreign body response, and impact of placing multiple valves.

8.2 Broader Impacts

Optimizing the design of physical devices requires long cycles of manufacturing, evaluation, and parametric analyses. This cycle can be reduced to some degree by the use of multi-physics simulators, such as COMSOL. However, even a sophisticated multi-physics simulator, which is very time-consuming itself, cannot factor in all the variables, especially when living organisms are involved. As such, the present disclosure outlines a framework for optimizing bio-mechanical systems with as few manufacturing and simulation cycles as possible. To this end, the present disclosure outlines interleaving the search for the best design parameters with surrogate model development. The search candidates are determined based on the model where only a subset of potential designs are simulated via COMSOL. The same selection process is repeated to determine even a smaller subset for manufacturing and testing. The models are continuously trained with each simulated or manufactured sample. The goal is to improve model efficacy in the vicinity of search samples while the accuracy can be sacrificed in other areas of the search space. The models are developed with the aim to relate manufacturing variables, such as physical dimensions or material composition, to various behavioral parameters, such as cracking pressure and reverse flow, both via benchtop measurements and via in vitro experiments. To enable extracting or otherwise constructing these models, in-vitro and in-vivo protocols can be used to optimize the overall system and determine the best non-invasive monitoring technique.

Foremost, the work outlined in the present disclosure will directly impact the design of biomedical devices. The model-based approach allows a design team to explore the entire design space for an implantable device prior to any fabrication or animal testing. This allows designers to explore a wider design space in their design optimizations and better understand trade-offs in the specification. While new types of implants or new applications for similar architectures will require significant effort to build accurate models, the potential to reduce the amount of physical fabrication and animal testing is considerable.

8.3. Overview

Figure 11A:
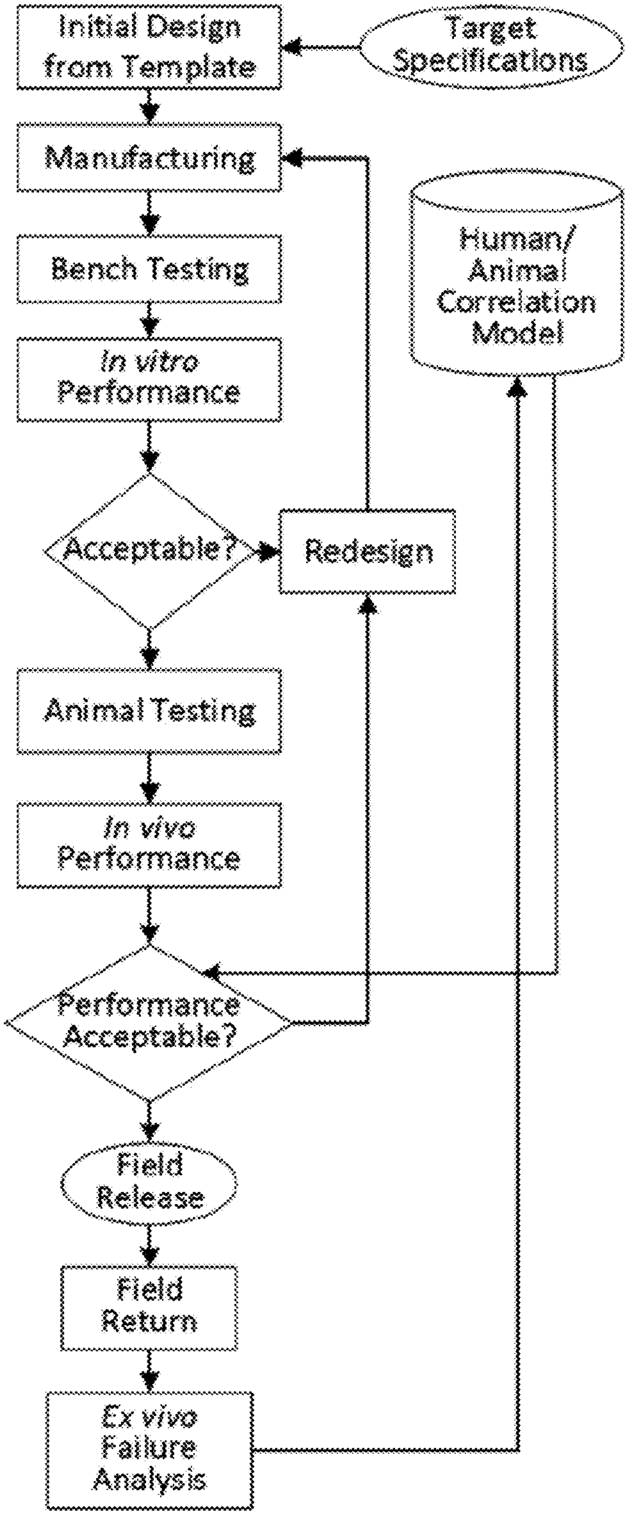
FIGS. 11A and 11B are a pair of flowcharts respectively showing an existing product design and use cycle for valve devices, and an improved product design and use cycle for valve devices according to embodiments of the present disclosure.
Figure 11B:
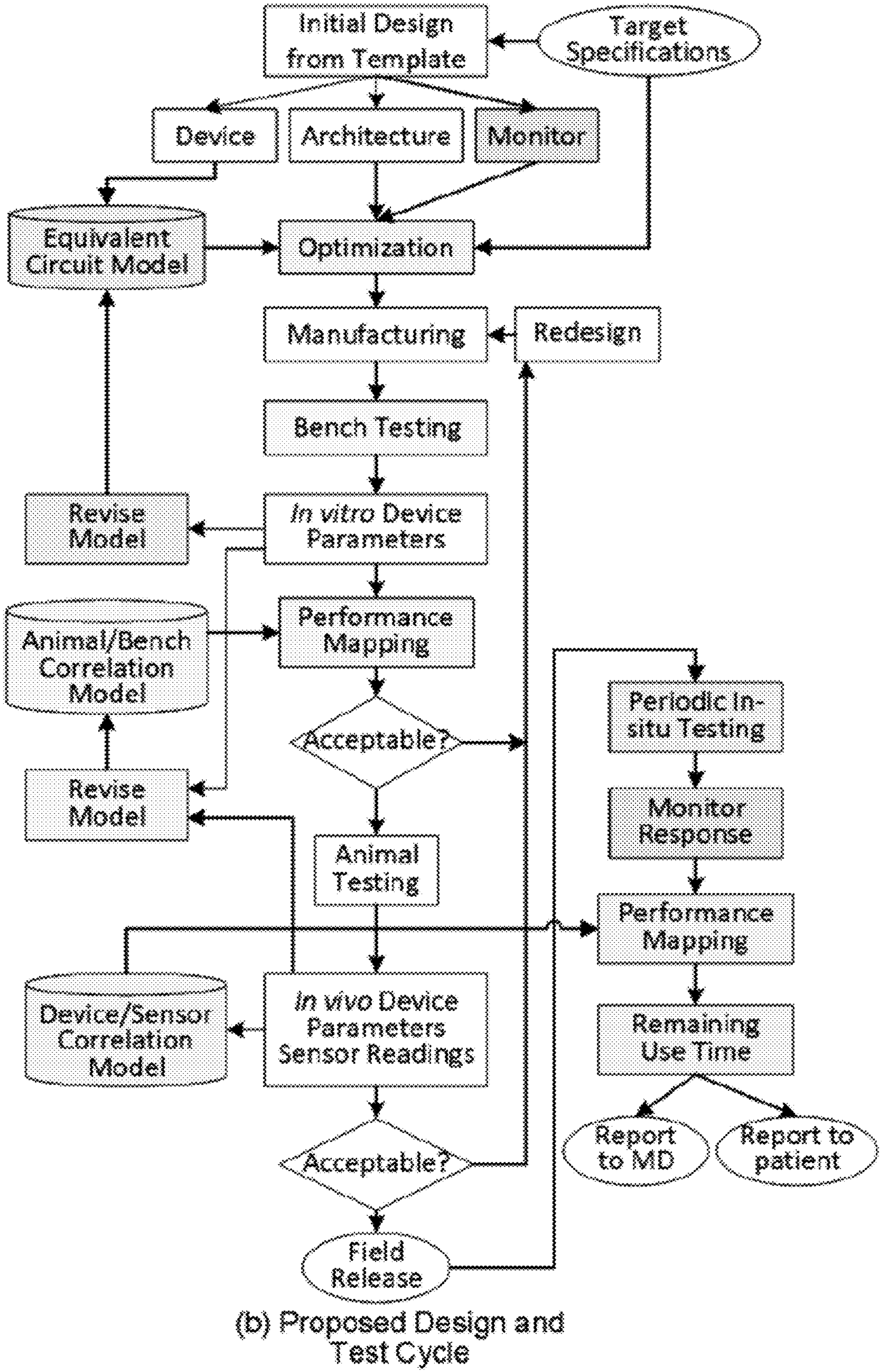

FIGS. 11A and 11B show comparison between a traditional flow for designing biomechanical medical devices and design automation flow outlined herein using equivalent circuit models and techniques developed in the domain of electronic design automation.

Traditionally, as shown in FIG. 11A, target specifications are used to select a potential design from the template. For instance, in the case of implantable valves, the design specifications can include cracking pressure and maximum size. The selected design template is manufactured and tested through a bench set-up, which tries to mimic real-life conditions. If the bench performance is not acceptable, another template needs to be selected or the existing template needs to be tweaked. This process is entirely ad hoc and is based on the expertise and experience of the designer, similar to the design process of analog circuits several decades ago. If bench testing is successful, the testing proceeds to animal testing. Pass/fail decisions and the process of redesigning after animal testing follow the same pattern. Once the product is released, there is no direct observability or controllability with regard to performance. It is removed after failure, which is diagnosed through patient discomfort. At present, failure analysis can only be conducted ex-vivo (e.g., after removal from the patient) to inform future designs. Unfortunately, this involves suffering for the patient, the reduction (and ultimately, elimination) of which serves as a primary motivator for the systems outlined herein.

In comparison, with reference to FIG. 11B, the present disclosure outlines an integrated design, testing, and monitoring procedure to improve the overall product quality and therefore patient well-being. As in the traditional flow, target specifications are used to select a design template. However, instead of focusing on the implantable device alone, the device structure, the overall architecture (including redundancies and implant locations), and the appropriate monitoring infrastructure (e.g. Doppler sensor or acoustic sensor) are examined together. The equivalent circuit model 420 (FIGS. 4A-5B) for the valve device is used to optimize performance of the device, both in terms of its functional parameters and in terms of its lifetime. Concurrently, the overall architecture incorporating the bodily system, including where and how the valve devices will be implanted and the monitoring electronics of the monitoring system 200 (FIG. 2) will be selected and optimized. After manufacturing and bench testing (e.g., by the testbench model 430), in vitro device parameters are obtained, which can be used to refine the equivalent circuit model 420. Another model (e.g., part of the behavioral model 320) linking in-vivo performances to in-vitro performances will be used to set the targets for in-vitro performances. If the performance is not acceptable, the entire system, including the device, architecture, and monitoring electronics can be redesigned with the help of the (refined) equivalent circuit model. This in-vitro process continues and repeats as necessary until the device parameters are satisfactory.

Next, the sample valve devices are implanted into animals and their in-vivo performance, as well as their degradation over a period of time, are evaluated. At this step, the response as obtained by the monitoring system 200 can also be recorded to further model the correlation between the device performance and the monitor response (in other words, to model correlation between indirect operational characteristics 312 and performance of the valve device reflected within parametric behavior characteristics 332). If necessary, the redesign process will be conducted using the improved models for device performances and monitor-to-device correlations. Upon field release, the entire valve system can be tested in situ, by instructing the patient to undergo several posture changes that generate an intracranial pressure gradient. The responses recorded by the monitoring system 200 will be used to correlate with device performance and an estimate of the remaining lifetime will be calculated. This information will be reported back to the patient as well as the healthcare provider. The predicted lifetime information is crucial for the healthcare provider to make decisions whether to remove the devices before they catastrophically fail. After device removal, an ex vivo failure analysis can be performed to improve the models and test limits for future designs.

As such, coupled development of a valve device and the monitoring system 200 can follow the design flow given in FIG. 11B. Since human trials are not feasible, the in-situ testing and analysis steps can be replaced with an additional step of animal testing where the test subjects are not constrained or sedated.

The monitoring system 200 (FIG. 2) of the present disclosure aims to incorporate regular valve assessment into the patient's daily activities to monitor the performance of the valves in-vivo. This data has the potential to provide peace of mind to the patient or parents of young patients by providing immediate feedback on the viability of the implanted valve. In addition, the assessments can be used to continually track the degradation and performance prior to the failure of the device. The data from these recordings can provide an assessment of the valve's viability over time which can be helpful to the physician in planning interventions and the manufacturer in improving models or finding outlier parts as well as manufacturing defects prior to any catastrophic patient outcomes. Currently, medical device manufacturers are only able to perform forensic investigations for failed devices ex-vivo after they have failed and have been removed from the patient.

8.4-8.5: EXAMPLES

In order that the invention described herein may be more fully understood, the following examples are set forth. It should be understood that these examples are for illustrative purposed only and should not be construed as limiting the invention in any way.

8.4.1 Fluid Mechanic Theory and Electronics Equivalency

Hydrocephalus is a buildup of excess fluid in the intracranial space causing an increase in pressure inside of the skull that results in excessive pressure on the brain. This pressure within the cranium (skull) is defined as intracranial pressure (ICP). The Monro-Kellie doctrine describes the relationship between volume and pressure within the cranium. It states the volume of blood, brain, CSF, and other components (e.g. tumors, hematomas, etc.) is constant within the in-elastic skull, thus an increase in volume of any one components must be associated with a decrease in one or more of the others. Blood and CSF, being fluids, can most easily compensate for increases in volume of intracranial contents. However, once their compensation mechanisms are exhausted, further increases in volume result in large increases in ICP. Shunt implants for the treatment of hydrocephalus implement a valve to help maintain ICP. These valves have diode-like one-way flow allowing excess CSF to exit the intracranial space when ICP rises above a given threshold, lowering the CSF volume and therefore lowering ICP. The pressure on the valve can be described by equations governing solid-fluid interactions described under the assumption of incompressible fluid flow, valid for liquids (as opposed to gas), for which the continuity equation for mass conservation becomes $\nabla \cdot U=0$. Furthermore, it is assumed that all flow in the system is pressure-driven which sets a number of constraints on the physics including a no-slip boundary condition. The pressure (P) within the cranium is incident on the valve resulting in a force (F) over the area (A) of the valve (P=F/A) which causes the valve to deform from a closed position into an open position, at a threshold called the "cracking pressure". Valve design and manufacture must meet requirements, dependent on patient anatomy and AAMI (Association for the Advancement of Medical Instrumentation) standards which set acceptable ranges for the cracking pressure. Valves actuated into the open position create a channel for the flow of CSF to distal locations (depending on shunt implementation). The flow of CSF through the valve has an associated volumetric flow rate, Q, defined as volume per time. The volume of CSF removed from the intracranial space is dependent on the time the valve spends in the open position, valve geometry, and the volumetric flow rate. The volumetric flow rate is calculated from the velocity distribution within the valve. CSF flow velocity in the z direction through a channel with cross-section in the x, y plane is defined for a horizontal location x in the channel as $$U_x = \frac{1}{2}\eta[y(h-y)]K$$

where $\eta$ is the viscosity, y is the vertical location in the channel, h is the height of the channel and K is the pressure gradient. Q, the volumetric flow rate, is determined by integrating all flow velocities throughout the cross-section. Which can be solved for rectangular cross-sections as:

$$\int_0^h U_x dy = \frac{Wh^3}{12\eta}K$$

where W is the width. This enables relation of the pressure difference between the two sides of the implant $\Delta P$ to the pressure gradient K by the length of the channel L as $K=\Delta P/L$. From these equations, the pressure difference across the channel can be related to the volumetric flow rate by the hydraulic resistance $R_h \Delta P=R_h Q$. This relationship is analogous to Ohm's law where the voltage difference across a component is equal to the current flow multiplied by its resistance. Hydraulic resistance can be defined as $$R_h = \frac{12\eta L}{Wh^3}.$$

8.4.2 Equivalent Circuit Models of Valve Operation and Hydrocephalus Physiology Given the established equivalency between the fluidic and electrical models, the equivalent circuit model 420 can be established to describe the implantable valve device. The equivalent circuit model 420 is a modification of the fluidic resistance in a rectangular channel based on the deflection of a rectangular membrane fixed at both ends for a width (w) greater than the length (l). The maximum deflection $$\delta_{max} = A(1-nu^2)\frac{\Delta P l^4}{Et^3} \text{ where } A = \frac{0.032}{1+0.4\alpha},$$

v is Poisson's ratio, E is Young's modulus, and t is thickness. This modifies the hydraulic resistance defined above $R_h$ for a rectangular cross-section based on the geometry of the deflected membrane as $$R_{cv} = \frac{12\mu l}{1-0.62\left(\frac{h}{w}\right)h^3 w}.$$

In addition, a capacitor is placed in parallel with the diode to model the compliance (susceptibility of a structure to move as a result of an external force). The capacitor is modeled as $$C_{cv} = \frac{0.032}{1+0.4\alpha^3}\frac{l^6(1-v^2)}{Et^3}.$$

This model establishes the behavior of a check valve modeled by the parallel combination of a diode and capacitor with a pressure gradient across the check valve modeled as a voltage difference, and the flow rate modeled as current. This model can establish that for the input pressure $P_{in}$ lower than the output pressure $P_o$, a closed valve, $$P_{in} = \frac{\Delta V(t)}{C} + P_o = \frac{1}{C}\int Q_{in}(\tau)d\tau + P_o.$$

The valve opens when $P_{in} \geq P_o + P_T$ where $P_T$ is the cracking pressure and the input pressure is equal to the fluidic resistance times the volumetric flow rate, so $$P_{in} = P_o + \frac{1}{C}\int Q_{in}(\tau)d\tau.$$

By incorporating this valve model into existing circuit models of hydrocephalus physiology, a full equivalent circuit model 420 for the valve and bodily system can be established. FIGS. 5A and 5B discussed above show one such electrical analog of the overall human hydrodynamics, as an extension of earlier work developing this model and a precursor to more recent work refining such models to include treatment modes. In the circuit diagram of FIG. 5A, the implanted shunt device releases fluid in parallel with the CSF outflow resistance. Components for this electric model of hydrodynamics: Cerebral blood flow (q); Pressure in the arterial ($P_a$), capillary ($P_c$), venous ($P_v$), venous sinus ($P_{vs}$) and intracranial ($P_{ic}$) compartments; Compliance of the arterial ($C_{ai}$), venous intracranial ($C_{vi}$), venous extracranial ($C_{ve}$), and tissue ($C_{tiss}$) elements; and Resistance of the intracranial arteries ($R_{ai}$), proximal veins ($R_{pv}$), distal veins and sinuses ($R_{vs}$), CSF formation ($R_f$), and CSF outflow ($R_o$) With a model for the system established, the system can be simulated to determine the impact of parametric changes. This provides the opportunity to use SPICE simulations to quickly model the system, and assess the effects of varying devices on the full physiology of the patient.

8.4.3 Preliminary Valve Design

8.4.3-1 Miniaturized Valve Designs

Figure 12A:
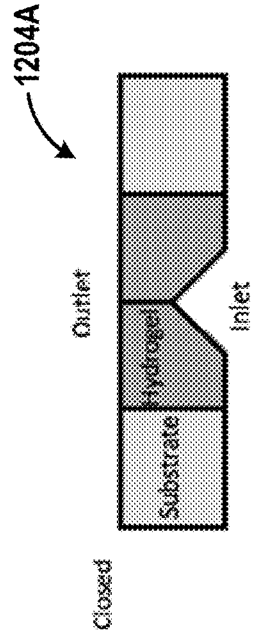
FIGS. 12A-12F are a series of diagrams showing operation of a hydrogel slit (FIGS. 12A and 12B), a diaphragm valve (FIGS. 12C and 12D) and a duckbill valve (FIGS. 12E and 12F).
Figure 12B:
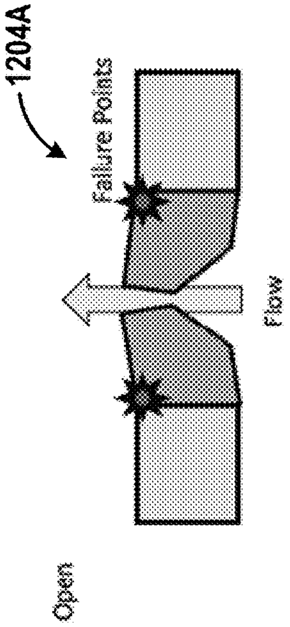
Figure 12C:
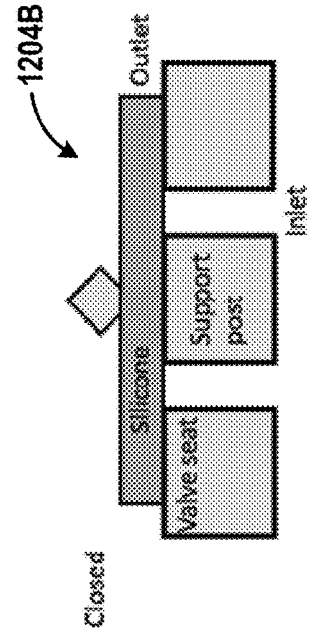
Figure 12D:
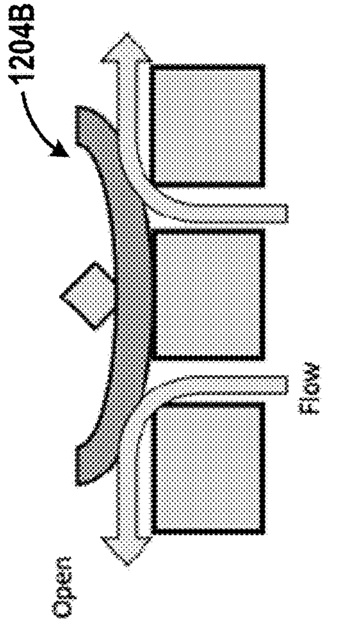
Figure 12E:
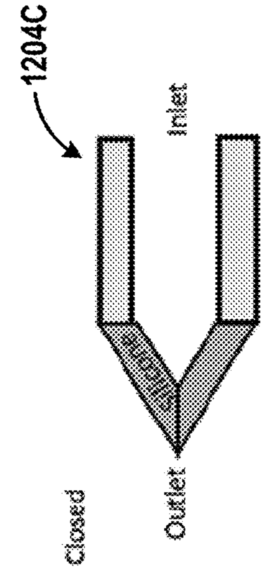
Figure 12F:
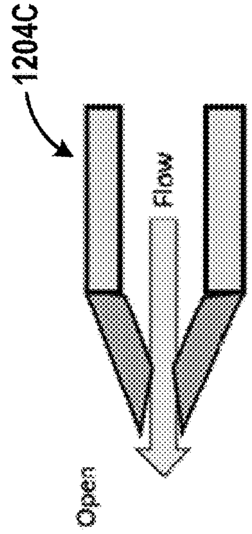

During preliminary study, a number of valve designs shown in FIGS. 12A-12F were explored for the treatment of hydrocephalus. Testbeds have been created to enable testing of the valves on the benchtop under a variety of conditions that mimic the intracranial space. The actuation of the valves has been observed under conditions of increasing and cycled positive and negative pressure to determine their performance. FIGS. 12A and 12B show simplified diagrams of a hydrogel slit valve device 1204A in a closed configuration and an open configuration. The hydrogel is cast in place on the substrate using a mold, then swollen by soaking in water. Hydrogel swelling ratio determines the force exerted by the leaflets pressing together along the central channel, thereby setting the cracking pressure. Asymmetric geometry sets the flow direction. FIGS. 12C and 12D show simplified diagrams of a diaphragm valve 1204B in a closed configuration and an open configuration. A positive pressure differential from inlet to outlet will deform the flexible silicone membrane, allowing fluid flow. Backpressure applied from the outlet will instead push the diaphragm against the valve seat, blocking flow. FIGS. 12E and 12F show simplified diagrams of a duckbill valve 1204C in a closed configuration and an open configuration. Positive pressure separates the leaflets, allowing flow. Reverse pressure pushes the leaflets together to block flow.

1) Hydrogel Slit Valve 1204A (FIGS. 12A and 12B): The hydrogel slit valves can be formed by fabricating two hydrogel leaflets that sit in contact in the absence of applied pressure. Hydrogel was selected as a means to create a positive and adjustable cracking pressure with a one-step manufacturing process (by creating internal stress during swelling in an aqueous environment). The two leaflets are asymmetric structures that separate with a small positive pressure. The asymmetry prevents small negative pressures from actuating the valve. The valves were formed using a 3D printed mold to cast hydrogel then embedded into a substrate (FIGS. 12A and 12B). The design was fabricated with both acrylic and glass substrates. The geometry of the inlet including the length and angle as well as the area of contact between the two leaflets all determine the cracking pressure. The hydraulic resistance in the open position is determined by the area of contact between the two valves and leaflet stiffness.
2) Silicone Diaphragm Valve 1204B (FIGS. 12C and 12D): Silicone was considered due to its excellent biocompatibility and resistance to degradation over repeated flexure cycles. Hydrogel was originally chosen for one-step manufacturing, but given the observed difficulties, the use of a two-step manufacturing (creating internal stress by deformation of separately-cast parts during assembly) was reconsidered.

A silicone diaphragm valve was designed using a thin membrane over a thick support structure with narrowed openings that increase the force on the membrane resulting from positive pressure resulting in actuation as shown in FIGS. 12C and 12D. Negative pressure forces the membrane onto the substrate preventing reverse flow. The thickness (i.e., stiffness) and diameter of the membrane along with the area of the openings and their distance from the center of the membrane determine the cracking pressure. The hydraulic resistance in the open position depends on the same parameters.

3) Silicone Duckbill Valve 1204C (FIGS. 12E and 12F): To further miniaturize the valve, an alternate design was tested using a silicone duckbill valve (FIGS. 12E and 12F). This simple design uses flexible leaflets which are pushed apart by forward pressure to allow flow or pushed together by backpressure to prevent backflow. As with the diaphragm valve, the cracking pressure of this valve design depends on the internal strain created during assembly of separate parts. The silicone duckbill valve is a check valve that resembles its namesake as shown. The bill has a tapered entry that increases the hydraulic resistance along the region of contact between the two leaflets that form the duckbill. The geometry of the taper, the area of contact between the two leaflets and the thickness of the leaflets determine the cracking pressure. The reverse hydraulic resistance of the valve in the open position is determined by the area of contact between the two leaflets as well as their thickness.

8.4.3-2 Potential Failure Mechanisms

There are several mechanisms for failure that are common to all implantable shunts as well as design specific valve designs that are dependent on the actuation mechanism. Generally, when a device is implanted, it is recognized as foreign and the body responds by attempting to isolate the foreign object by forming scar tissue. This can result in a valve that is permanently held in the closed state by the tissue.

In addition, biofilms and biological materials (cells, proteins, etc.) can accumulate on the surface of the implants that can result in shifts in cracking pressure, changes in the hydraulic resistance, or catastrophic failure. As described in Sections 8.5.1 and 8.5.2, the hydraulic resistance defines the relationship between pressure and flow and is therefore critical to the function of the shunt. This is, in fact, the primary cause of failure that results in a gradual decrease in performance over time that eventually fails catastrophically when the shunt becomes clogged. Unfortunately, the clogs must generally be resolved through surgical methods requiring the patient to undergo a craniotomy (opening of the skull) that carries high risk.

Static and reverse flow leakage results in unwanted flow through the valve for pressures at or below zero which are ideally zero flow, especially with small magnitude negative pressures. If the diodicity, ratio of pressure drop in back flow pressure drop in direct flow is low or static leakage exists, the potential for unnecessary drainage of CSF increases which could result in harmfully low ICP.

Other mechanisms for failure include mechanical failure of the valve itself. These failures are also generally associated with degradation over time ultimately resulting in the valve fixed in either the closed or open position. Both states are dangerous to the patient resulting in excess pressure buildup (fixed closed) or over-draining of CSF (fixed open) and potential entry of substances into the intracranial space. More closely examining the failure mechanisms, three categories are defined: unseating of the valve from the shunt, actuator failure, and materials failures. Unseating of the valve occurs when the valve actuation mechanism remains intact, but the valve itself detaches or shifts significantly within the shunt housing causing failure of the shunt. Actuator failure results from the components of the valve the actuate becoming damaged over time and no longer open and close as expected, and finally the materials failure can occur in shunts due to aging or degradation of the material in the system that are not designed to actuate or deform rather they provide some necessary structural element of the shunt. Several types of valves are detailed herein to provide more concrete examples of valve performance and failure.

As is the case with traditional electronic circuit manufacturing, bio-electro-mechanical systems are subject to defects in the manufacturing process as well. Some defects are readily observable after manufacturing and are easy to detect. Other defects may cause changes in the device parameters. In order to investigate the effect of out-of-tolerance process variations, a parameter (the valve length) of a set of functioning valves (FIGS. 13A-13C) was intentionally varied. The valve length was varied from 3 mm down to 1 mm. At the shortest length, a reverse flow leakage was observed.

Figure 13C:
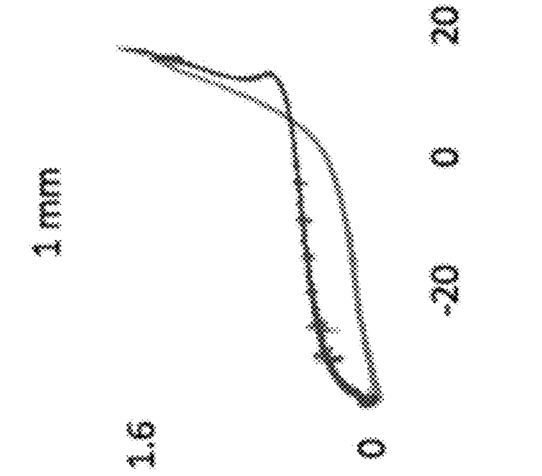
FIGS. 13A-13C are a series of graphical representations showing an effect of manufacturing variation on the duckbill valve pressure-flow behavior.
Figure 13B:
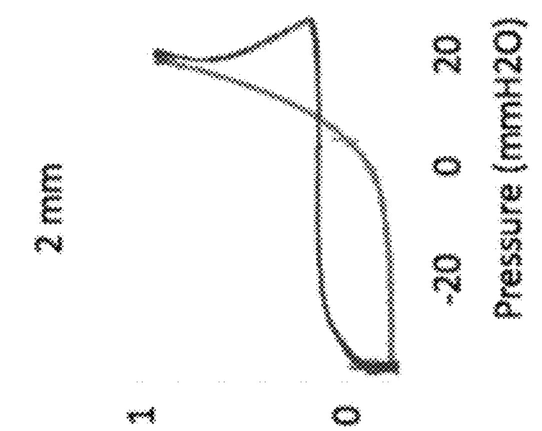
Figure 13A:
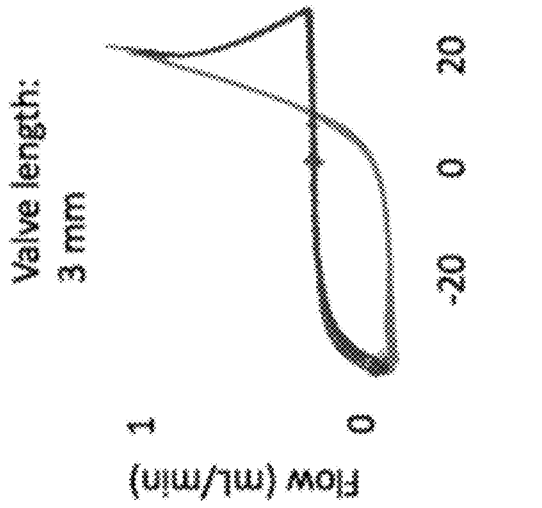

FIGS. 13A-13C shows the effect of manufacturing variation on the duckbill valve pressure-flow behavior. The cracking pressure on the rightmost edge of the increasing-pressure (dark curve) phase is reduced slightly from 3 to 2 mm and is reduced dramatically from 2 to 1 mm. The lighter curve shows decreasing pressure.

Figure 14A:
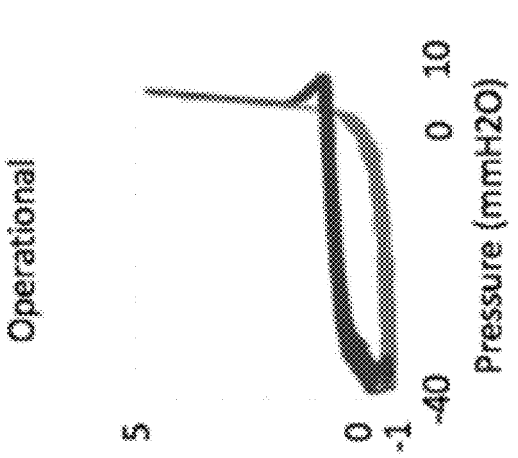
FIGS. 14A-14C are a series of graphical representations showing testing results from duckbill valve prototypes.
Figure 14B:
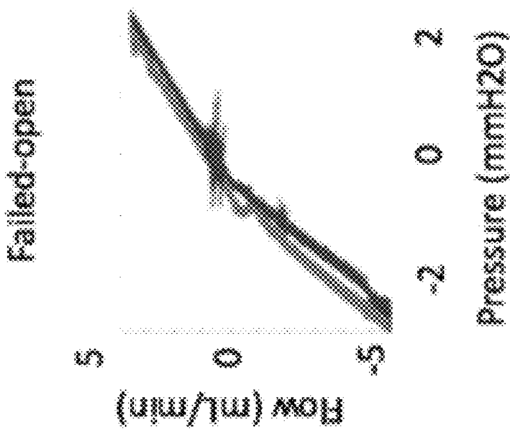
Figure 14C:
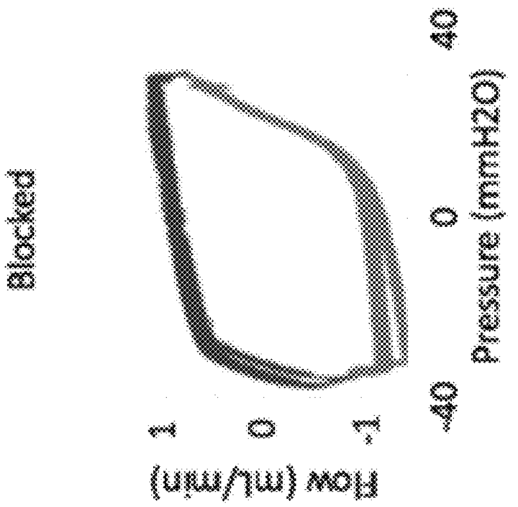

1) Hydrogel slit valve 1204A (FIGS. 12A and 12B): The hydrogel slit valve described above was tested with both acrylic and glass substrates. This improved the hydrogel bond strength to the substrate and thereby extended the valve lifetime by ~50%. This work also included computational modeling of hydrogel stress and fluid flow during valve opening. High stress was predicted at the attachment points where the hydrogel meets the supporting substrate. This model was corroborated by post-failure imaging of a cross-section of the hydrogel valve, which showed that the hydrogel detached from the glass substrate at the outlet-side attachment point. This may be due to compression during valve opening or due to tension during application of backpressure when closed. Both the lifetime and parametric failure (shift in cracking pressure) were observed.
2) Silicone Diaphragm Valve 1204B (FIGS. 12C and 12D): One design used a silicone (PDMS—polydimethysiloxane, Sylgard 105) diaphragm placed onto a 3D printed valve seat and support structure (PLA resin printed, Formlabs 3). For testing, this printed support was inserted into a section of tubing to allow for application of positive and negative pressure and measurement of the resulting flow (measured by Omega PX26-001DV sensors, Analog Devices DAQ, Labview Signal Express). The complexity in manufacturing and disparate materials led to highly variable performance from valve to valve. The implementation also suffers from low volumetric flow rates resulting from the stiffness of the diaphragms.
3) Silicone Duckbill Valve 1204C (FIGS. 12E and 12F): Design-specific failure mechanisms for the duckbill design include propensity for clogging due to the high hydraulic resistance of the valve leading to poor diffusion near the interface between the leaflets. In addition, the valves form a cantilever-like structure that may deform under conditions dependent on the pressures at the distal end of the shunt resulting in variations in valve performance. FIGS. 14A-14C show testing results from duckbill valve prototypes, with FIGS. 14B and 14C showing measured behavior of example failure modes (manufacturing failure). Blue: increasing pressure phase of cycle; Red: decreasing pressure.

As shown in FIGS. 14A-14C, the blocked valve appears to show some non-zero flow—this is due only to measurement artifacts (tubing compliance, allowing flow by expansion and contraction of the tubing connecting the valve to the pressure sources and sensors). The operational/functioning valve also shows this artifact. The failed-open valve (middle) does not show this artifact because the high flow prevents any buildup of pressure. The operational/functioning valve also shows a nonlinear effect during the increasing-pressure phase (blue): the resistance drops immediately after opening, causing a temporary reduction in pressure below the cracking pressure while the flow increases. This behavior—a pulse occurring at a specific pressure—may be useful in external monitoring as a signature of valve opening.

8.4.3-3 Behavioral Manifestations of Failure Mechanisms

A. Catastrophic Failures

Figure 15:
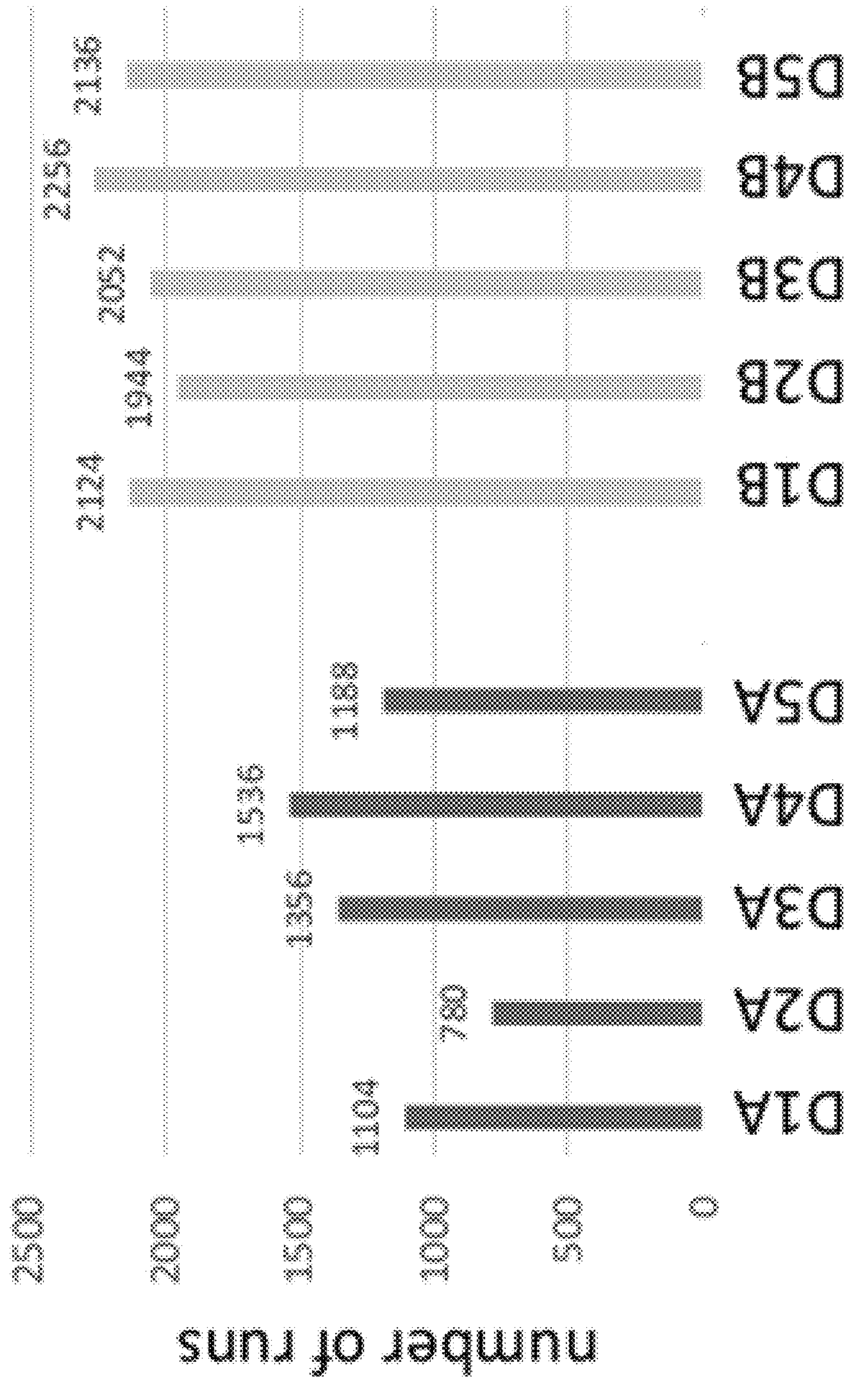
FIG. 15 is a graphical representation showing lifetime before failure for two sets of 5 hydrogel valves on differing substrates (acrylic vs. glass)

Catastrophic failures can stem from any of the aforementioned mechanisms manifesting as a complete functional failure. The valve can either be stuck open or shut under a catastrophic failure. In order to investigate the catastrophic failures, a testbed was implemented for determining valve performance under repeated actuation cycles. From these data, the expected lifetime as well as the mechanisms for failure can be observed. As noted earlier, FIGS. 14A-14C show possible responses during catastrophic failure modes of the silicone duckbill valve. The operational valve (FIG. 14A) shows the desired behavior of opening at positive pressure and closing at negative. The failed-open valve (FIG. 14B) shows an equally low resistance at both positive and negative pressures (note that only a small pressure difference is needed to produce large flow). The failed-closed valve (FIG. 14C) shows near-zero flow across the full range of positive and negative pressures tested. Results from extensive testing of the hydrogel check valves is shown in FIG. 15, which shows results from two sets of 5 hydrogel valves on differing substrates wo substrates (acrylic shown in D1A-D5A and glass shown in D1B-D5B) of the valve were tested before failure with the results from five of each design (1-5) both designs demonstrated variability in lifetime. Lifetime was assessed as the number of open/close cycles until reverse leakage occurred.

Catastrophic failures are easier to detect as they result in very discernible change in device behavior as well as extreme discomfort for the patient. However, the goal should be to avoid catastrophic failures and intervene before failure occurs.

B. Parametric Failures

As noted earlier, various failure mechanisms result in changes in device behavior before eventually resulting in a catastrophic failure. These failures are categorized as parametric and the manifestation of the failure modes on the device behavior are investigated.

Figure 16A:
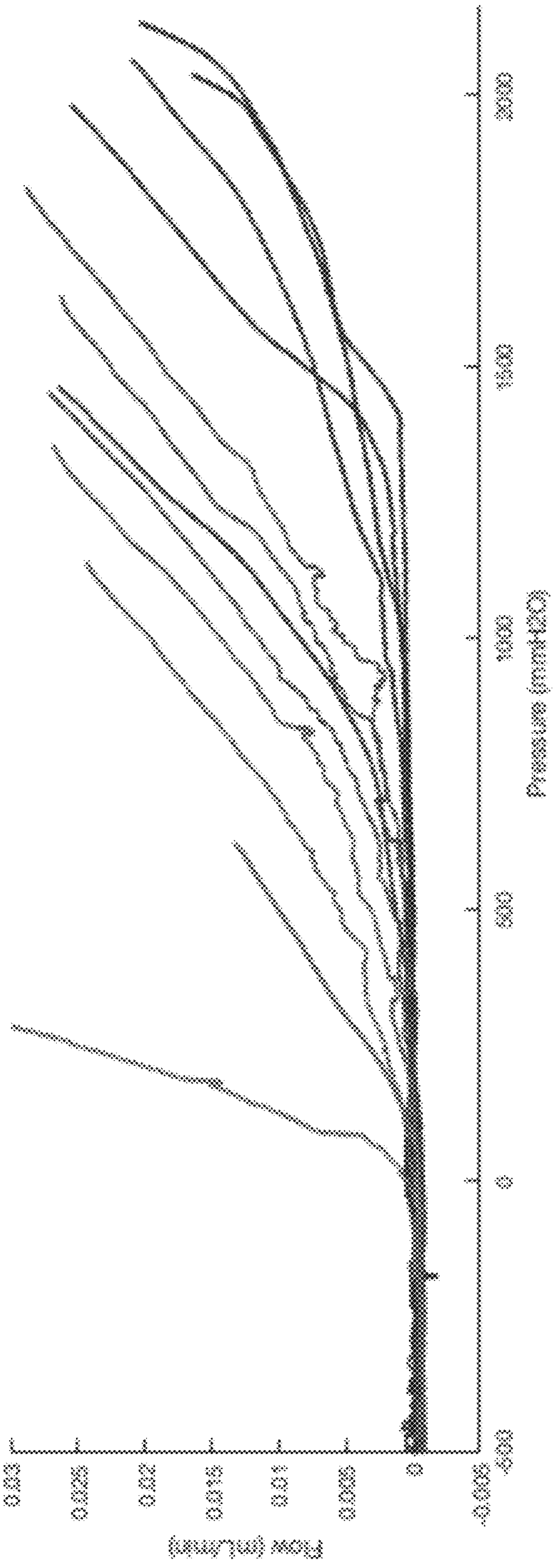
FIG. 16A is a graphical representation showing long-term analysis of the pressure-vs-flow through the hydrogel valve.
Figure 16B:
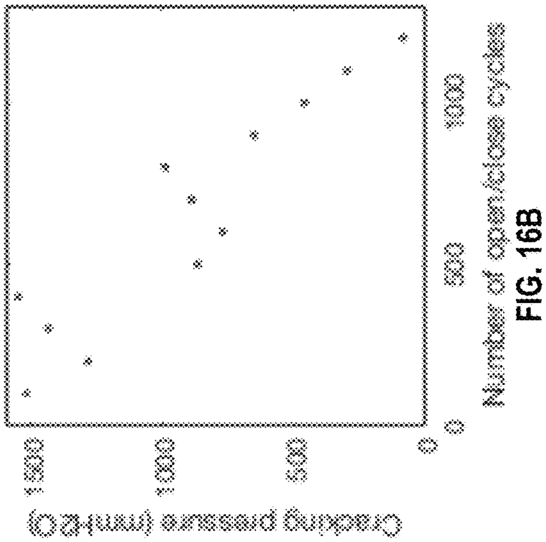
FIG. 16B is a graphical representation observed change in cracking pressure of the hydrogel slit valve across repeated open/close cycles.

1) Decrease in Cracking Pressure: Material breakdown at the valve base could result in mechanical failure and result in a decrease in the cracking pressure. In order to demonstrate and model this behavioral manifestation, pressure-flow behavior of the hydrogel valve was tested to failure over 1300 open-close cycles (FIGS. 16A and 16B). Each separate curve corresponds to data recorded approximately every 100 cycles. Blue curves recorded at the beginning of testing, red curves towards the end (immediately before total valve failure). It was observed that the cracking pressure decreased linearly as the valve aged. This represents a parametric failure of the valve which will lead to overdrainage of CSF, causing symptoms including severe headache. In subsequent imaging, the failed valves showed detachment of the hydrogel from the supporting substrate. Near failure, the valve resistance also appears to decrease (seen as an increased slope of the flow-pressure relation in the leftmost curve).

FIG. 16A shows long-term analysis of the pressure-vs-flow through the hydrogel valve. Only the increasing-pressure phase of the pressure cycle is shown for clarity. Measurements were taken immediately after manufacturing (blue line, near the right edge of the plot), and then re-taken after approximately 100 cycles of increasing/decreasing pressure to actuate the valve and the valve aged towards failure (red line). FIG. 16B shows observed change in cracking pressure of the hydrogel slit valve across repeated open/close cycles. Cracking pressure approximated as the pressure corresponding to 5 μL/min flow. Cracking pressure dropped near-linearly over time, approaching zero. This shows parametric failure of the valve. No reverse leakage was observed.

2) Increase in Cracking Pressure: Build-up on the valve or its surface may reduce the flexibility of the valve and/or increase its mass, making it harder for the valve to respond to pressure build-up. In terms of device behavior, this failure mode results in an increase in the cracking pressure. This is due to a biological response of the body to the foreign object which can only be observed once the device is implanted in a host. However, theoretically, it is deduced that this kind of build-up will increase the cracking pressure.

Manufacturing variation may also produce an increase in cracking pressure. FIGS. 13A-13C discussed above show the change in cracking pressure as valve length is varied: longer valve leaflets have a higher cracking pressure, visible as the rightmost extension of the blue curve before the negative resistance opening occurs.

3) Increase in Reverse Flow Rate: Build-up of biological material around the valve can prevent the valve from properly closing, resulting in an increased reverse flow rate. Similarly, a valve incorrectly mounted on its seat will also manifest as an increase in the reverse flow rate. In the diaphragm valve, the curved valve seat creates a resting deformation by pressing against the silicone diaphragm. This deformation of the membrane during assembly is necessary in order to create a nonzero cracking pressure and thereby prevent reverse leakage at negative pressures. FIGS. 17A-17D shows the effect of a manufacturing defect in the silicone diaphragm valve which allows for reverse flow. Such a defect may be detected in post-production testing.

Figure 17A:
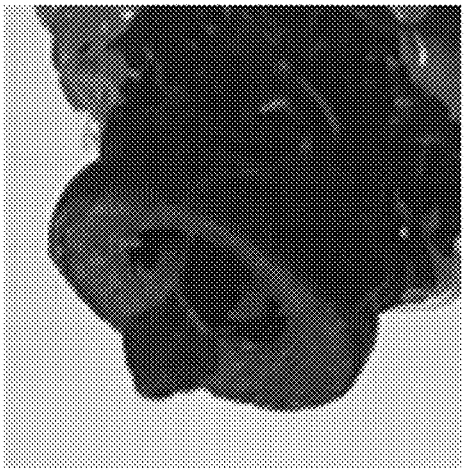
FIGS. 17A and 17B are a pair of images showing a curved valve seat and associated behavior of the curved-seat valve.
Figure 17B:
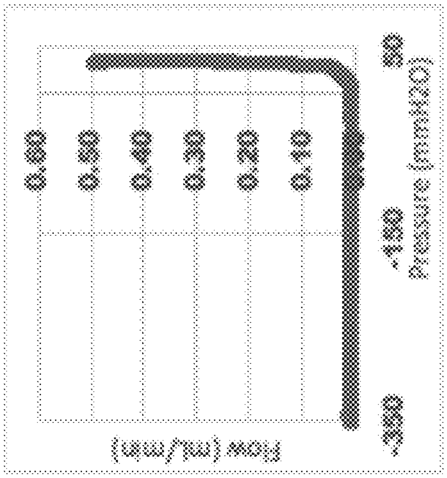
Figure 17C:
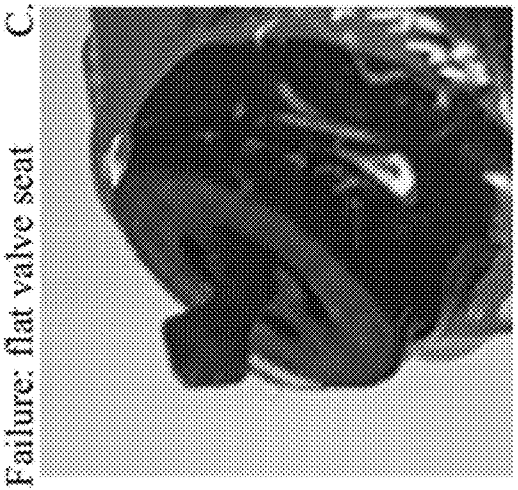
FIGS. 17C and 17D are a pair of pair of images showing a flat valve seat and associated behavior of the flat valve seat.
Figure 17D:
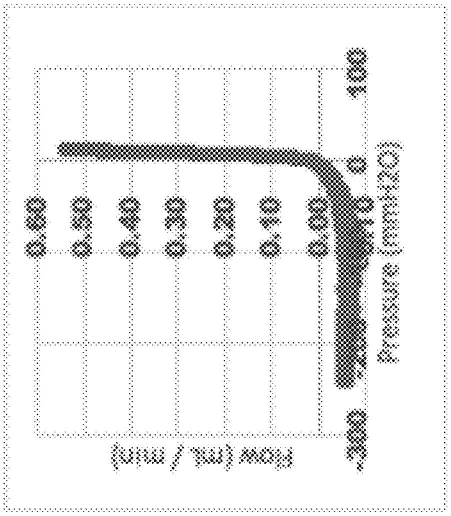

With reference to FIGS. 17A-17D, two designs for the diaphragm valve support are shown without the silicone diaphragm over the center post. FIG. 17A shows a curved valve seat, and FIG. 17B shows behavior of the curved-seat valve, showing near-zero reverse leakage. FIG. 17C shows a flat valve seat, and FIG. 17D shows the resulting pressure-flow behavior of the flat-seat diaphragm valve, showing considerable reverse leakage at negative pressures.

4) Detection of Parametric Failures: The aforementioned failure mechanisms manifest first as parametric deviations in the device behavior before resulting in catastrophic failures. In order to prevent any adverse effects on the patient, parametric failures need to be detected in a timely manner. Since the valve is implanted, periodically testing the valve under controlled conditions is not possible. Similarly, the valve is controlled by a physical stimulus and is not accessible to an electrical stimulus that can be generated in-situ. However, the investigation of the failure modes has demonstrated that all the identified manifestations cause a change the pattern of the cranial pressure.

Figure 18:
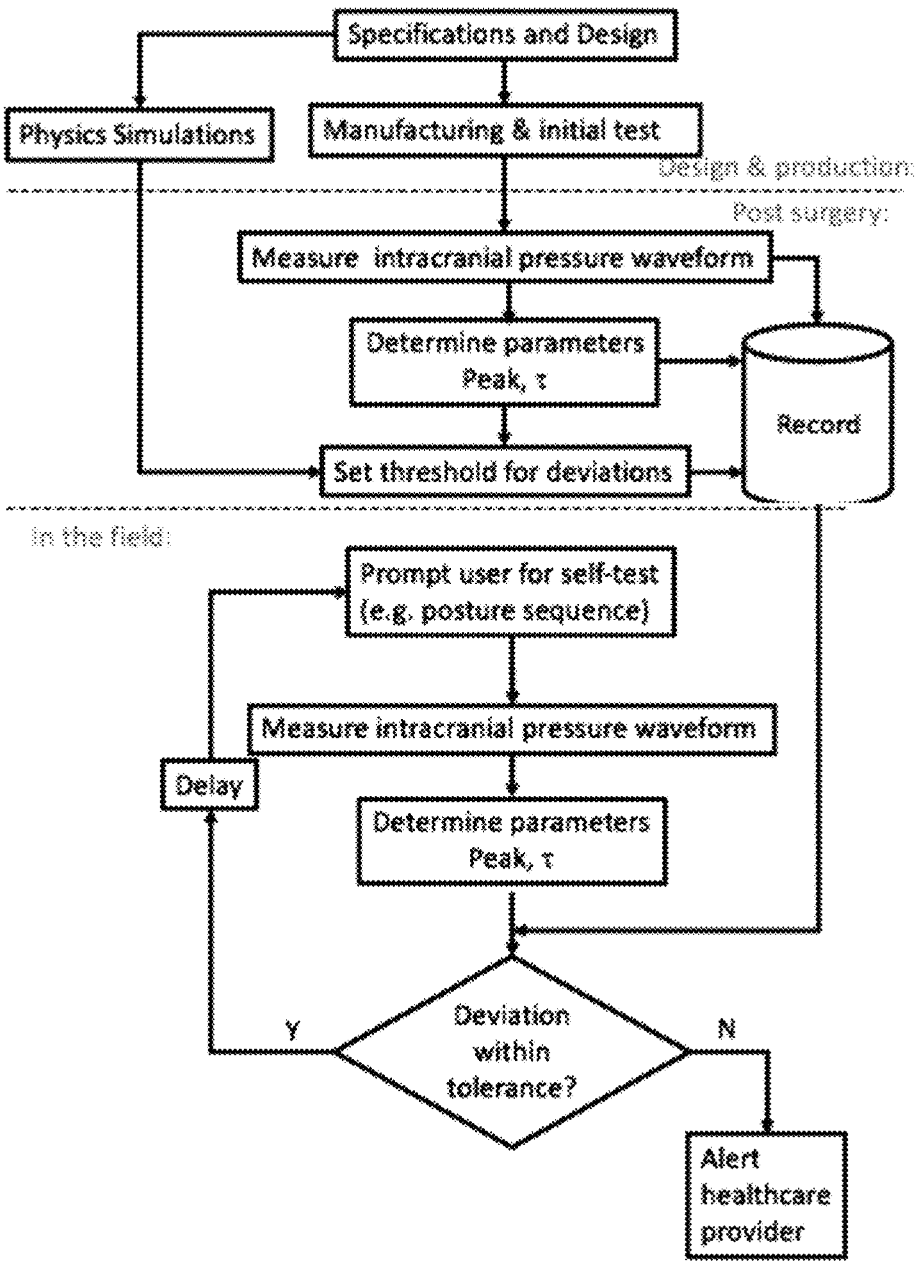
FIG. 18 is a process flow chart showing an in-situ human-in-the-loop development and testing procedure for a valve device in accordance with aspects of the present disclosure.

Increased cracking pressure will increase the peak intracranial pressure observed. Decreased cracking pressure will reduce this peak. Increased reverse flow rate will not change the peaks, but will result in faster build-up and therefore more frequent opening and closing of the valve or slower reduction in the pressure. Thus, if the cranial pressure is observed via an implanted pressure sensor, the peak pressure as well as the time constant of the pressure waveform will change. However, these values also depend on the movement and position of the patient. In order to remove this variable from the testing process, the patient needs to be instructed to take a specific position (such as laying down or standing up) which would, under normal circumstances, generate a repeatable cranial pressure signal. FIG. 18 shows an example human-in-the-loop test method that may be applied to monitor functionality of a valve device using the monitoring system 200 shown in FIG. 2. The present test method relies on this waveform to determine if the device is functioning within normal parameters.

Figure 19B:
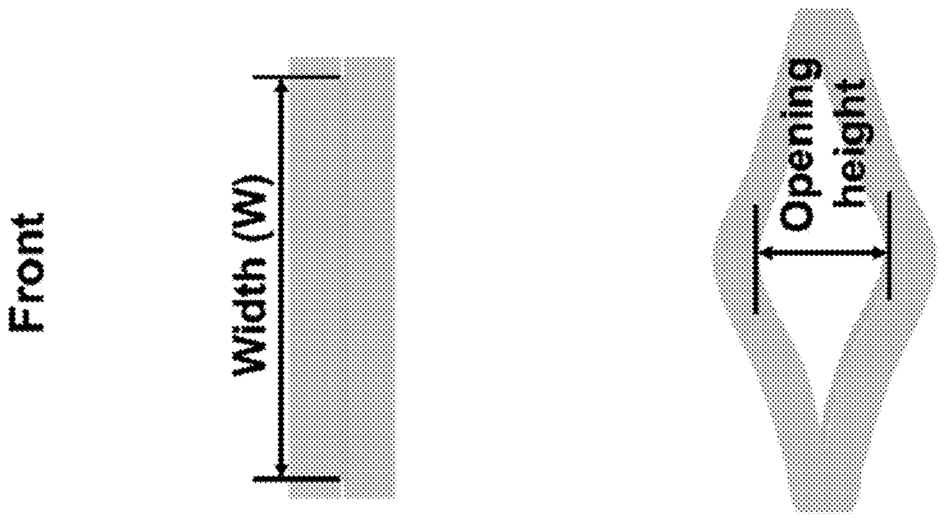
FIGS. 19A-19C are a series of images showing an effect of adjusting valve parameters on valve behavior, where
Figure 19A:
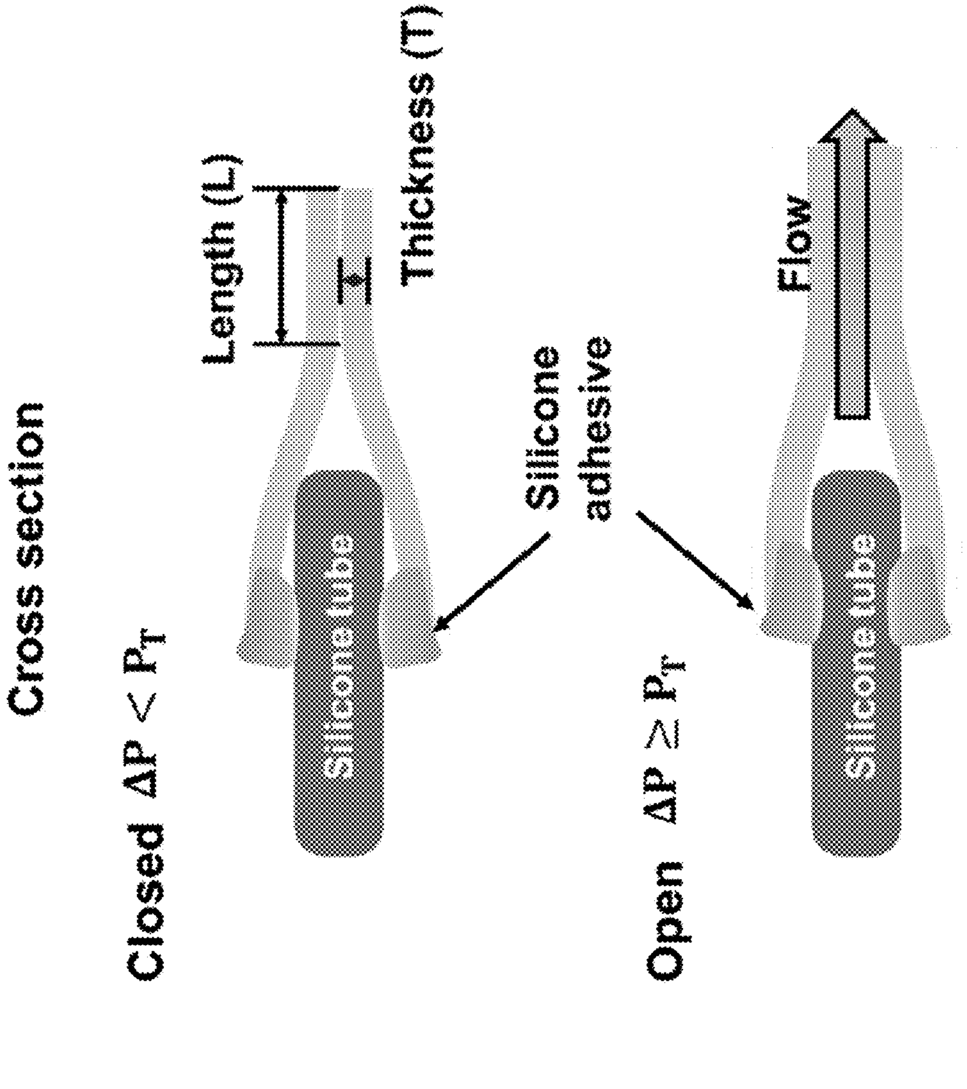
Figure 19C:
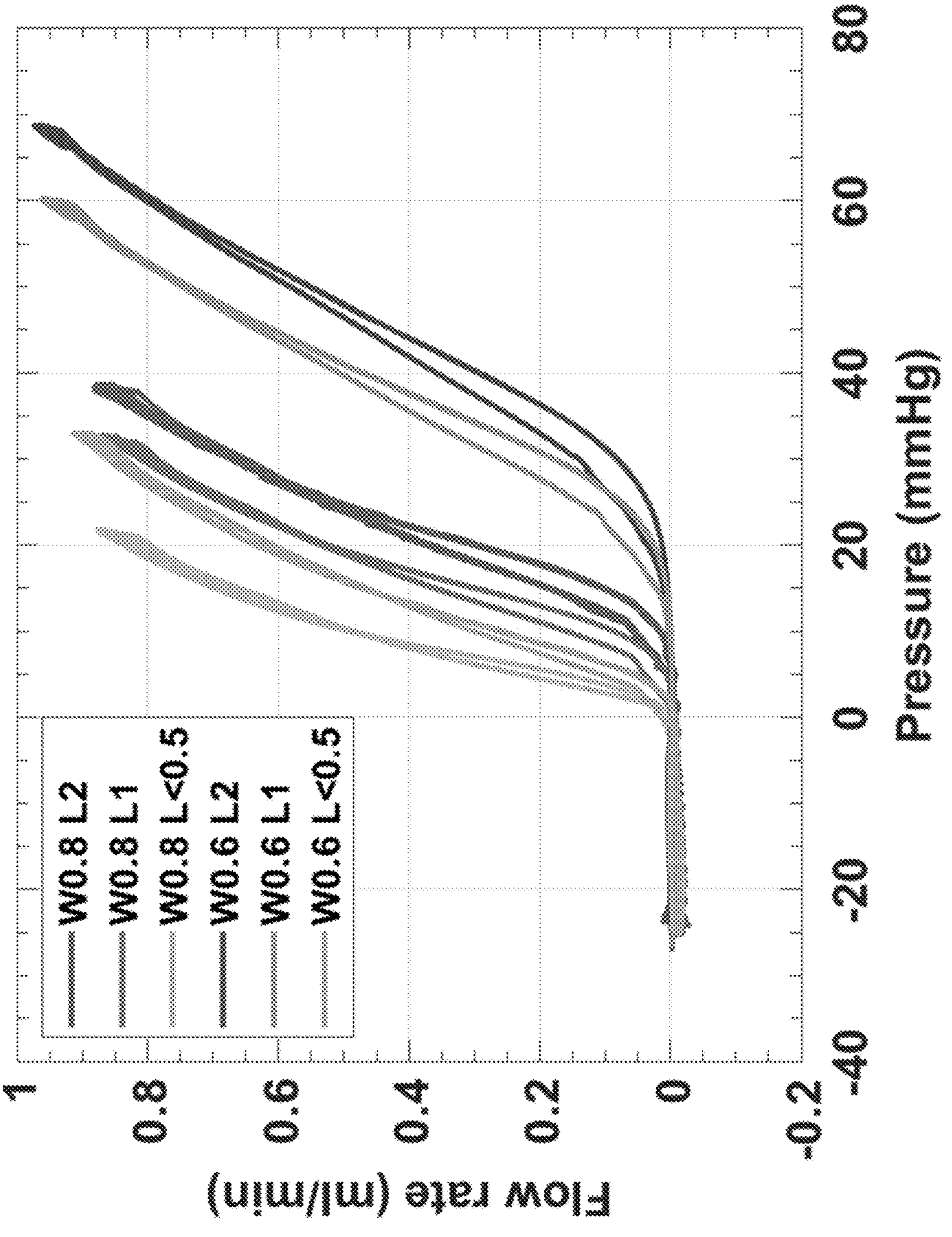

A miniaturized valve shown in FIG. 1B is considered for the treatment of hydrocephalus. Unfortunately, the breadth of the design space made it impossible to investigate all of the architectures, materials, and geometric designs and variations possible within the design space. In addition, inducing hydrocephalus in a rodent is an inconsistent process, leading to uncontrolled variability. However, a test-bench setup is established for long-term testing of microfluidic valves using both pressure and flow-driven mechanics. This setup was used to observe the performance of microfluidic valves with varying geometry as shown in FIGS. 19A-19C.

Figure 20B:
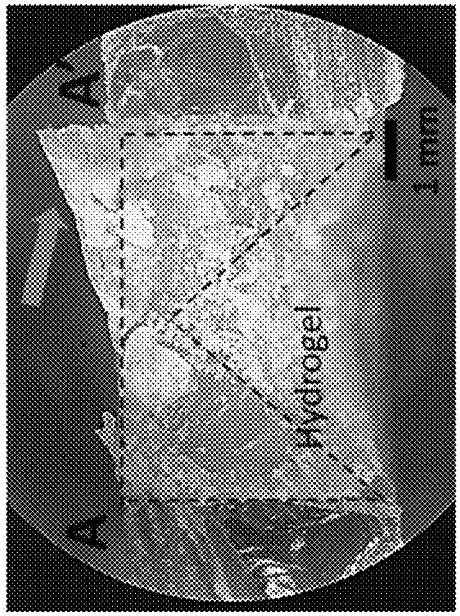
FIGS. 20A and 20B show failure analysis of a hydrogel-based valve, where
Figure 20A:
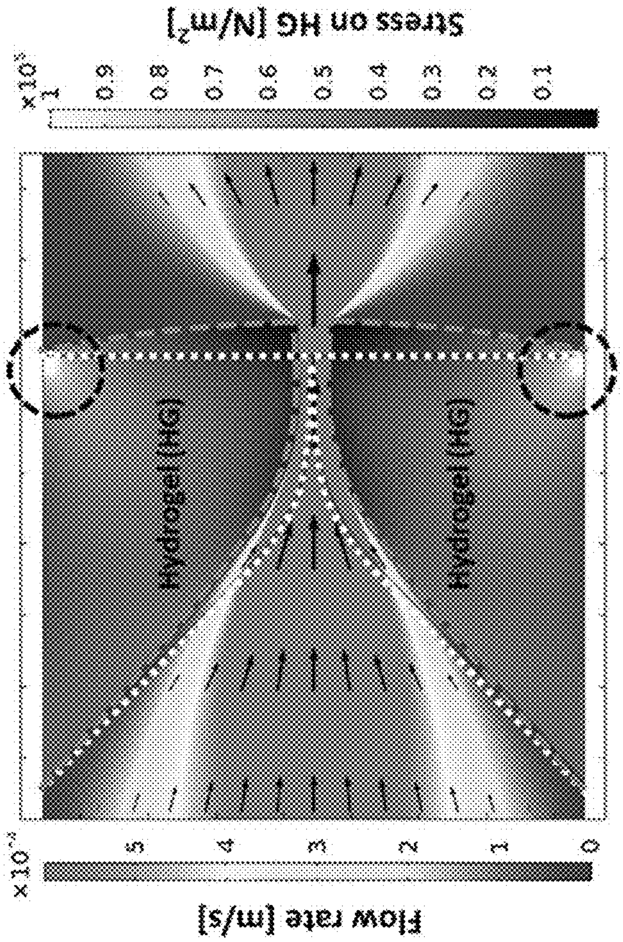
Figure 21A:
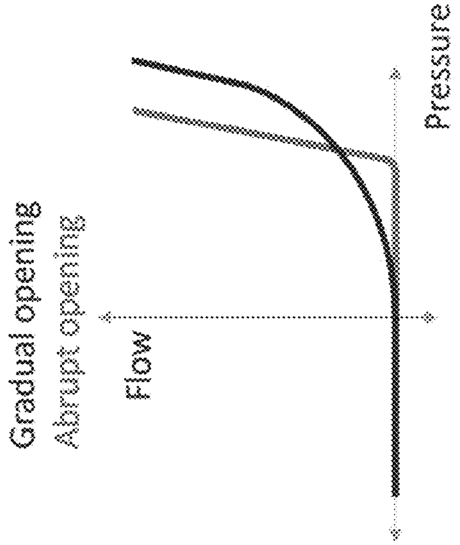
FIGS. 21A-21G are a series of images showing a design space for varying valve opening and closing behavior, where
Figure 21B:
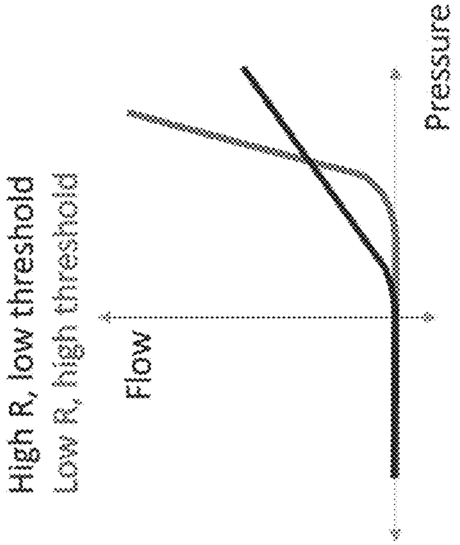
Figure 21C:
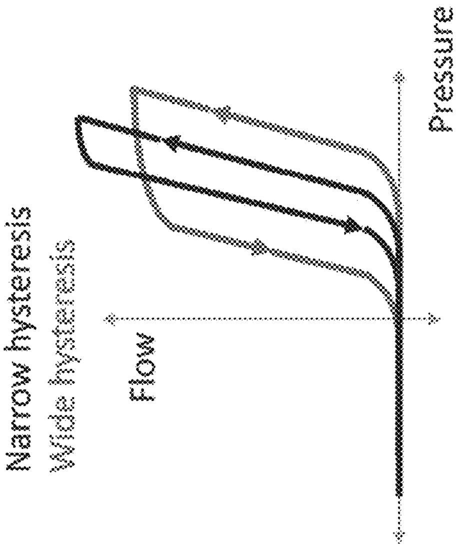
Figure 21D:
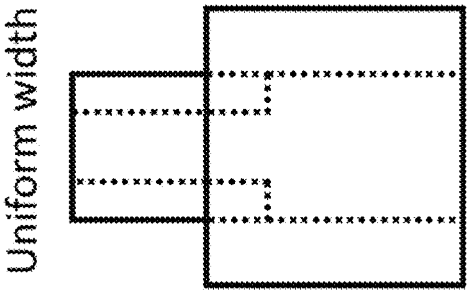
Figure 21E:
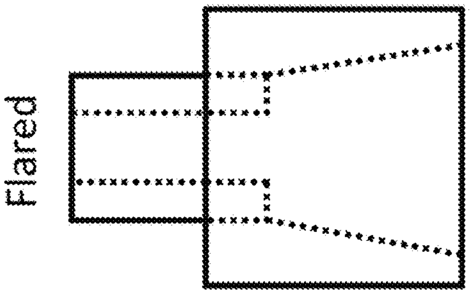
Figure 21F:
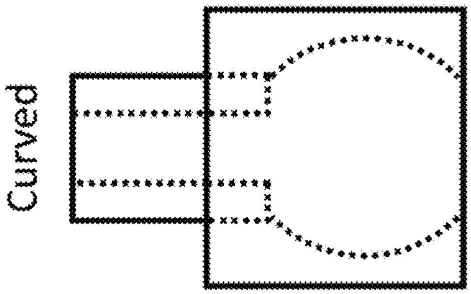
Figure 21G:
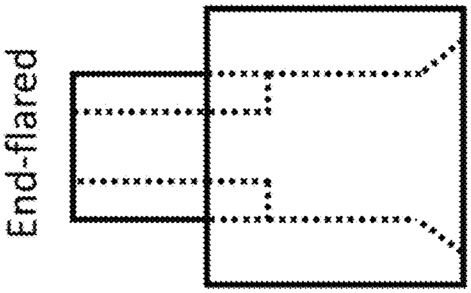

In addition to assessing the cracking pressure and pressure-flow characteristics, the degradation of the valves and the failure mechanisms were observed. The degradation in behavior shown in FIGS. 20A and 20B (as well as FIG. 16A) is particularly noticeable.

8.4.3-4 Failure Prediction System

Beyond the standard clinical methods of shunt assessment (e.g. MR imaging and infusion studies), alternate means to detect failure of shunts have been explored. One option includes using ultrasound to observe movement of the valve mechanism inside the shunt. Note that the flow of CSF is not directly visible on ultrasound (conventional or Doppler), since CSF has no scattering particles. Instead, the ultrasound monitors the movements of the valve during pressure changes. The resulting images can be used to accurately distinguish between normal flow, proximal obstruction, and distal obstruction of the shunt.

Passive RF backscatter sensors may provide another means to interrogate the operation of implanted valves, with minimal extra volume of electronics required for incorporating the sensor into the valve. Such wireless systems can send low-fidelity recordings of neural activity with minimal onboard passive components and a small RF antenna. Merging this class of sensing and telemetry with biomechanical devices could yield a passive bio-electro-mechanical (BEM) device.

The failure prediction system can provide a number of distinct advantages over current methods in that it could be used for daily monitoring of shunt performance to monitor the behavior of the device over time. A combination of prediction methods and frequent monitoring could prompt intervention prior to catastrophic failures by self-observed or parent-observed symptoms.

A. Human-in-the-Loop Testing

A known issue with shunt flow observation is that, at any particular time, the shunt may be fully operational but simply not passing fluid. This issue underlies the need for exogenous fluid infusion tests. However, the posture and position of the user can also affect the pressure across the shunt. This is well-studied in standard shunts which run from the head to the abdomen (ventriculoperitoneal shunts). Standing up lowers the pressure in the head as compared to the abdomen, which can result in excessive drainage termed the siphon effect. Many standard shunts include a posture-dependent anti-siphon valve to reduce this risk of over-drainage.

Alongside noninvasive valve behavior monitoring, the system may prompt the user to perform an intentional sequence of postures and/or exercises (e.g. a Valsalva maneuver) as a means to apply a test sequence of pressure changes across a device. Such a self-test procedure could be performed on a regular basis much more readily than the standard clinical methods of shunt assessment (e.g. MR imaging and infusion studies). Any noninvasive self-testing procedure would require a measurable proxy of the valve behavior which is sensitive to the possible valve failure modes. Furthermore, the ubiquity of smart phones would enable concurrent measurement of position, motion, and ICP to track the statics and dynamics of the motion.

FIG. 18 mentioned above shows a flow diagram of a human-in-the loop test method for monitoring the operational health of the implanted valve according to aspects of the present disclosure. Design parameters of the valve will be determined based on the specifications. Once the valve design is complete physics-based simulations can be conducted to determine the limits of parametric variations (e.g., using a suitable application such as COMSOL Multiphysics® or another suitable application). This information will be used later to determine acceptability limits for changes in the intracranial pressure waveform. The manufactured designs will be characterized during post-production test phase to filter out defective components. However, some components with parametric defects as well as latent defects may escape this process since manufacturing testing cannot fully duplicate the use conditions. After the valve is implemented into the body, an initial set of tests are performed via the built-in pressure sensor. This step will determine the parameters of the fresh valve in its mission mode environment. These parameters consist of the peak of the pressure waveform as well as its time constant and will be stored for comparison. After deployment, the patient will be prompted at regular intervals to take various test positions and the intracranial pressure waveform is recorded. The parameters of the waveform are compared with the initial readings. Based on the thresholds determined from simulations at the design phase, it can be determined whether the device has degraded beyond the acceptable limits.

8.4.4 Design Automation

Once the valve device and surrounding bodily system is modeled in terms of an analog electronic circuit, existing design optimization approaches can be leveraged to optimize the performance and lifetime of the overall system, which includes the sensing interface and may include redundant devices. The cost function in the optimization will include factors for treatment efficacy (maximum pressure before the valve opens), size of the external sensing interface (which introduces additional complexity during use), and the longevity of the overall system.

Analog design automation has been a challenging task due to highly complex relations, large design space, and multiple constraints that are generally in trade-offs. Analog design automation approaches can be categorized as model-based (knowledge-based) approaches and simulation-based approaches. In model-based methods, analytical expressions between circuit parameters and system performances are used within the context of the search for the optimum design parameters. With the model in place, the design optimization problem can be framed as a convex optimization problem, which can be solved with standard search techniques. As opposed to model-based techniques, simulation-based methods directly evaluate the performance of a design sample using simulators, such as SPICE. Various global optimization algorithms including simulated annealing (SA), particle swarm optimization (PSO), evolutionary algorithms, such as genetic search, differential evolutionary algorithms, and gradient-based local search with multiple starting points (MSP) have been proposed. These algorithms generally avoid getting stuck in the local minima thanks to their stochastic behaviors.

For the optimization of bio-mechanical devices, deriving analytical models relating design parameters to performance and reliability parameters would be a daunting task. Thus, analytical model-based approaches will not be applicable to solve this problem. Simulation-based approaches would require a large number of multi-physics simulations, which are computationally very costly. Thus, methods that utilize a large number of simulations are also not applicable. A third class of design optimization approaches relies on surrogate models that are generated based on simulation data. The modeling techniques include support vector machines (SVM), artificial neural networks (ANNs), and Gaussian process (GP). Due to the high computational cost of EM simulations (similar to multi-physics simulators), these hybrid approaches have been popular for design optimization of antennas and antenna arrays. Since the problem described herein has similar challenges to the antenna design optimization problem, this domain can be leveraged to develop an optimization algorithm based on a surrogate circuit model of the valve device and its environment (e.g., the bodily system).

8.5. Modeling Approach

Biomechanical Modeling Approach: In this aim, a fluidic model of the rodent anatomy and implantable valve can be constructed based on the human anatomical equivalent circuit model 420 discussed above with reference to in FIGS. 5A and 5B. This equivalent circuit model 420 enables use of classic circuit modeling techniques and tools to investigate the system. Highly optimized circuit-specific tools such as Monte Carlo simulations can be employed to explore variations in both the anatomical and engineered components of the system. This enables exploration of a highly-dimensional, wide dynamic range design space. To validate the results from the equivalent circuit model 420, finite element analysis is used to investigate complex multi-physics in the system. Finite element modeling (FEM) is inherently more computationally intense, thus the design space is reduced via circuit design tools prior to validation with finite element modeling. Empirical results will inform the refinement of behavioral models and design choices for the valve device in an iterative manner.

Step 1.1—Determine the design and model parameters for the device and environment, the design space, and define the cost function for the optimization of the device behavior and reliability.

Step 1.2—Build and analyze the structure of the equivalent circuit model (surrogate model) for the valve and surrounding anatomy. Develop a search-based optimizer that will select device samples (sets of design parameters) that optimize the device behavior.

Step 1.3—Build and analyze a finite element model (FEM) for the valve and surrounding anatomy.

Step 1.4—Using the results of the FEM simulator for the selected device samples and the surrogate circuit response, improve the models through several iterations Test bed for long-term fluidic in vitro studies: Completed simulation studies inform the fabrication of valve devices for evaluation on the test bench. Empirical testing approaches will further narrow the design space and validate simulation results. These studies can be approached in a fluidic test bed (testbench model 430 of FIG. 6) to implement long-term studies that enables placement of fabricated devices into a system that can repeatedly actuate the valve devices to determine life-time and failure mechanisms.

Step 2.1—Increase the channel count for our benchtop fluidic test bed and verify performance.

Step 2.2—Implement a test protocol that mimics the postural pressure changes in the animal model.

Step 2.3—Upgrade existing benchtop fluidic test bed to include capability for oxidative stress and thermal control.

Step 2.4—Complete fabrication of prototypes and broad study of the design space; use results to refine the circuit model and FEM (as per milestone 1.4).

Step 2.5—Use benchtop results to select devices for animal testing, allowing further iteration of the models.

Step 2.6—Use the results from the broad search to validate models, use optimizer output to determine the most informative parameter spaces to search.

Step 2.7—Return to equivalent circuit model and simulate designs based on optimizer recommendations.

Step 2.8—Evaluated the equivalent circuit model results with the objective function to determine which designs to simulate in FEM.

Step 2.9—Use FEM results to refine the optimizer's translation between all models.

In vivo studies with in situ monitoring: Valve devices will be tested in a rodent model to determine the performance relative to the benchtop and simulation models. This will enable further refinement of the models, including behavioral model 320. In addition, the use of in-situ monitoring of the devices though minimally-invasive means as in the monitoring system 200 can be implemented and tested, using both the Doppler ultrasound and acoustic sensing modalities. The models (including the in-vitro models and the behavioral model 320) can be further refined based on the data from the in-situ sensing and performance of the devices can be mapped to the simulation and benchtop models. Furthermore, animal testing enables examination of complex responses that will not be present in either the simulation or benchtop models such as inflammation due to surgical trauma, foreign body response, and impact of placing multiple valves.

Step 3.1 Determine an in vivo testing protocol that enables in situ monitoring of the valves and flow during positional changes.

Step 3.2 Complete testing of single devices with monitoring, enabling us to map performance to the simulation and benchtop models.

Step 3.3 Complete testing of animals with multiple devices implanted and repeat testing.

8.5.1 Development of Equivalent Circuit Model

Referring to the equivalent circuit model 420 shown in FIGS. 5A and 5B, model parameters for the equivalent circuit model 420 can be determined based on literature, simulation, and empirical results (benchtop and in vivo). During design space exploration, appropriate model components may be added based on deviations of both the simulations and empirical results. Several valve geometry parameters are demonstrated in FIGS. 19A-19C, alongside measurements of the resulting pressure-flow behavior of the various valve designs; these will serve as a basis to fit parameters to the model. Beyond these basic parameters (length, width, and thickness), the design space allows for nonuniform channel width as shown in FIGS. 21A-21G. These channel variations would alter the opening and closing kinetics of the valve, and also affect the fluid velocity profile as shown in the FEM simulation in FIGS. 21A-21C. Note that fluid velocity can significantly affect the tissue response to the implant: shear stress is known to be an important factor affecting the scar tissue occlusion of conventional hydrocephalus catheters. Broader parameter variations include the duckbill material (bulk stiffness, surface energy) the inlet tubing (length, diameter, and wall thickness), and multi-valve approaches (two or more valves placed in the same surgery, where the valves may have different behavior).

Within the defined parameter space, the structure of the equivalent circuit model 420 for the valve and surrounding anatomy can be built and analyzed. A search-based optimizer can be constructed to determine a set of device implementations defined by the design parameters for simulation. The simulation result can be used to improve the surrogate models, while the surrogate models are used to iteratively select the next set of device samples. By interleaving the search and modeling steps, developed models are more accurate within the vicinity of search samples while accuracy in other areas of the search space may be sacrificed. The efficacy of this modeling approach will be verified by comparison with models based on randomly generated samples.

8.5.2 Bench Testing and Evaluation of Physical Device Samples

Bench testing of manufactured samples is a crucial step in evaluating device performance as well as optimizing the device design. During bench testing, the devices are placed in a simulated environment of changing fluid pressure as in FIG. 6. Bench testing aims to accomplish several goals for development of valve device designs as well as the behavioral model 320 of the monitoring system 200:

Characterize device performances: Cracking pressure and reverse flow can be measured to characterize the performance of each valve device and the variations in device performance from one cycle to another (reproducibility of the behavior).

Characterize reliability parameters: Devices can be subjected to continuous stress in the form of pressure build-up and release, emulating their behavior in the normal mode of operation. However, the rise time and frequency of the fluid pressure changes will be much faster compared to the normal operation, resulting in accelerated aging. This process, enables characterization of mean time to failure as well as parametric degradation in the device performances (cracking pressure and reverse flow) over time. This process will also help in modeling operational defects. For instance, this process enables determination of whether failures result in "always-on" or "always-off" behavior, or catastrophic changes in cracking pressure and reverse flow. In addition to increased frequency, reactive accelerated aging (RAA) can be applied by modulating various parameters including the temperature and oxidation of the test fluid.

Characterize dynamic behavior: The dynamic behavior of the devices can be characterized by applying a step input (i.e., fluid pressure) or input with a steep rise time. Dynamic characterization can also be achieved by changing the frequency of the input signal until the device can no longer respond, analogous to a frequency sweep of a linear time-invariant circuit. This testing will enable us to generate more accurate circuit models for the device. Further, characterizing the dynamic behavior enables correlation with posture information 314 at deployment of the valve device and the monitoring system 200.

FIG. 6 discussed above shows an example testbench set-up to test and evaluate the device samples, which enables measurement of the cracking pressure and flow through the valve device. This basic setup can stress the valve device under constant flow and evaluate the point at which it fails. In some examples, the testbench model can include equipment to heat the system to perform testing at body temperature or higher. Medical devices are commonly tested by accelerated aging using immersion in heated saline. Heating increases the rate of any degrading chemical reactions, according to the exponential dependence of the Arrhenius law. However, heated saline alone does not fully model the hostile environment created by the immune cells recruited in the foreign body response. Reactive Accelerated Aging (RAA) is a recently-developed method for aggressively testing the degradation of neural implants under biologically realistic stresses. This method uses hydrogen peroxide to reproduce the generation of reactive species during the brain's immune reaction to implanted devices. At the elevated testing temperature of 87 C, the hydrogen peroxide degrades with a half-life of 23 minutes. Knowing this, (unheated) concentrated hydrogen peroxide can be injected into the test fluid to maintain the target concentration of 10-20 mM. Accelerated aging will enable the characterization of both the device reliability parameters and the failure-predicting signals within a reasonable amount of time.

8.5.3 Design Space Exploration and Design Optimization

The valve and the bodily system design involve several parameters that need to be optimized. The physical parameters include: (a) overlap between the inlet tube and the valve, (b) silicone durometer, (c) length and width of the valve, (d) height of the channel in the valve, (e) inlet tube length and diameter, (f) outlet exit angle. Furthermore, the selection of each parameter also influences process variability; smaller dimensions and steeper angles lead to higher process variations. At the architecture level, design choices include: (a) the number of valves to be implanted, (b) the relative parameters of each valve, (c) the placement of valves, and (d) valve-integrated sensing or system-wide sensing. Finally, for the monitor design, the design parameters include: (a) sensing modality (e.g. ultrasound, radiofrequency, pressure, acoustic), (b) receiver design requirements in terms of sensitivity and noise figure, (c) excitation signal strength (e.g. ultrasound), (d) frequency of excitation, (e) dynamic range requirement, (f) battery life, and (g) size and cost of the sensing product Decisions in terms of architecture, monitor, and device parameters are interrelated, requiring an overall optimization process. In electronic circuit design, the optimization process relies on fast and accurate circuit simulators to explore the design space. Unfortunately, for the design of the bio-mechanical system, an overarching simulator that can evaluate the overall performance in a reasonable amount of time does not exist. Device parameters can be simulated using the COMSOL multi-physics simulator. While COMSOL provides accurate results in terms of rigidity and dynamic mechanical response, it cannot be relied upon to simulate the entire system. In order to model the degradation pattern and the reliability of the valves based on the physical parameters, manufacturing and extensive testing are still necessary. Furthermore, COMSOL cannot be used to run the many simulations that the optimization process would require, due to the computational cost.

As such, the necessary circuit and system models can be developed, as well as an overall optimizer framework to co-optimize system, monitor, and device parameters with as few COMSOL simulations and as few manufacturing and lab testing cycles as possible. FIG. 4B discussed above shows the flow and main components of a framework for development and optimization. Three levels of simulation/ emulation can be used to evaluate the performance of a potential design. The costliest evaluation technique is the manufacturing and testing of physical samples, as such, it is desirable to limit this to a small number of samples. Multiphysics simulations of device samples using the COMSOL simulation environment can be used for a larger number of samples. While more efficient than physical manufacturing and testing, COMSOL simulations still take a long time. Therefore, it is desirable to avoid COMSOL simulations as much as possible during the optimization process, particularly early on when samples are generated based on diversity as much as based on potential performance. A particularly efficient simulator is based on the equivalent circuit model 420 of the device, which can be included in a MATLAB simulation environment (or equivalent software) along with architectural decisions and the choice of the monitoring modality. Therefore, MATLAB simulations can be relied upon heavily to optimize the circuit parameters.

Circuit models for the device can be extracted based on templates generated by the research team. The models can be trained on both COMSOL simulation samples and physical samples that are bench-tested. The selection of samples for manufacturing and testing will be similar to a genetic search. Early in the search, diverse samples are preferred. As the optimization process progresses, samples with the highest likelihood of success will be selected for manufacturing. Monitoring modalities and architecture templates are supplied to the optimizer. The number of choices for architecture and monitoring modalities is limited. However, these choices have a significant impact on the overall performance of the system. Their impact also depends on the device parameters. Thus, for each device sample, a different architecture and monitoring modality may be selected. A MATLAB model will be generated for system-level simulations to evaluate the system performance in terms of functional and reliability parameters as well. The optimizer is a search engine that takes as input, the generated samples and the overall performance and selects the new set of samples that will potentially minimize a cost function defined based on system performance

8.5.4 In-Situ Human (Animal) in-the-Loop Testing

Animal models can be used for testing which most closely mimics testing in human subjects. Given that it is not particularly viable to test the devices in humans, a rodent model is selected to inform the valve models and benchtop testing approach. Valve geometries selected in Aim 2 can be implanted into rat hydrocephalus models. Once the valves are implanted, the intracranial pressure can be monitored directly using wireless sensors. In addition, non-invasive monitoring as in the monitoring system 200 can be performed using both acoustic and Doppler sensing. The implanted pressure sensors will serve as a ground truth measurement to determine the accuracy and sensitivity of the non-invasive measures as well as accuracy of inferences made by the behavioral model 320 of the monitoring system 200. One wireless monitoring system (Kaha Sciences, NZ) has been selected that enables gathering continuous data from sensors implanted into animals while they are freely moving.

The rodent surgery will require a craniotomy (opening in the skull) through which kaolin may be injected. Kaolin has been established as a method of inducing hydrocephalus in rodents. Following the kaolin injection, the valve(s) will be place in the rodent. The craniotomy will be closed with a low durometer cement as recommended by the manufacturer of the telemetry system. The wireless sensing system will allow us to gather data continuously post-surgery. In addition, the animals will be periodically monitored with non-invasive sensors as in the monitoring system 200. The animals will be rotated from level to 90 degrees (head up) three times and negative 90 degrees (tail up) three times with the non-invasive monitor placed on the rodent head to induce posture changes. The posture changes will generate a change in the intracranial pressure that will be reflected in both the implanted ground truth ICP measurement and the non-invasive indirect wireless measurement obtained using the monitoring system 200. FIGS. 3B and 3C demonstrates changes in ICP from rat experiments with implanted pressure monitoring. The effect of posture is visible as a change in ICP of several mmHg. This method provides the ability to induce significant pressure changes in a repeatable manner without any pain or distress to the animals.

In addition, specimen behavior can be observed through a motion-activated camera setup and recording of various biological signals. The implanted pressure sensors provide continuous streaming of ground-truth data from the freely moving specimen. The rat will be encouraged to change positions (lie down, stand up, move around) by placing food and water at different locations in the set-up. Furthermore, this data will enable extrapolation from an animal model to consider the human use case in understanding how critical the positional calibration would be to monitoring the implantable device viability and intracranial pressure.

8.5.5 Animal-Bench Correlation Model

Bench measurements that define the performance of the device, namely cracking pressure and reverse flow, need to be correlated to the behavior of the device embedded into a live specimen for development of the behavioral model 320 of the monitoring system 200. This correlation will be used to set and update the design optimization goals. In-Situ Human (Animal)-in-the-Loop Testing Protocols (Section 6.4) will be used to continuously measure the intracranial pressure while the time-stamped camera recordings will be used to correlate the pressure signal to the positional information of the specimen. In order to aid with determining the time indices where the position of the specimen has changed, an existing animal behavior observation system, which was developed for detecting the behavior of multiple marine megafauna can be modified. By monitoring the ICP directly, the cracking pressure of the implanted valve device can be inferred. Furthermore, hysteresis parameters can be determined by correlating the movement of the specimen to the measured intracranial pressure. These in-vivo measurements will then be correlated to the benchtop in-vitro measurements. For statistical modeling, simple basis functions will be explored, such as polynomial, sinusoidal, or Gaussian. More complex modeling methods, such as machine-learning-based models, require extensive data and may be less efficient (but are not completely infeasible, especially as machine-learning methods and computer hardware improve over time).

The correlation model between the in-vitro and in-vivo measurements along with the reliability studies that record the device behavior over time (under overstress) in-vitro will be used to determine the remaining lifetime of the device once in-field measurements are done. Further, modeling incremental changes in cracking pressure and reverse flow based on incremental changes in monitor response can be explored. Incremental degradation modeling for micro-electromechanical devices has been shown to provide much higher accuracy compared to predicting device behavior through indirect measurements.

8.5.6 Device-Sensor Correlation Model

Measurement of intracranial pressure directly with pressure sensors requires an invasive process which we would like to avoid. The valve's behavior based on the fluid pressure also generates auxiliary signals, which can be detected by a Doppler sensor or an acoustic sensor as indirect operational characteristics 312. FIG. 3A discussed in an earlier section herein shows an illustration of how Doppler and acoustic sensors can capture the device's behavior externally. The dotted curve shows the intracranial pressure as the subject changes position repeatedly. As the pressure builds up, the valve opens to let the cerebral fluid drain and closes once the pressure is relieved. The cerebral fluid flow can be detected during the time that the valve is open via Doppler ultrasound (solid gray curve). The opening and closing of the valve also generates a sound signal which can be detected via an acoustic sensor, plotted as a solid black curve. To build the behavioral model 320, all three signals need to be present, and will be measured in the animal experiments (Section 6.4). Once the data are collected, measured signals can be correlated to other parametric behavior characteristics 332 including cracking pressure and reverse flow. After implanting the devices in patients, direct ICP measurements will not be available. However, by observing indirect operational characteristics 312 including the acoustic and Doppler signals through the same series of movements in the patients over time, it will be possible to monitor the changes in the device behavior using the incremental degradation models by inferring values of parametric behavior characteristics 332 (Section 8.5.5).

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A valve monitoring system, comprising:

a sensor that generates a signal expressive of indirect operational characteristics of a valve device, the valve device being positioned between a first cavity and a second cavity of a bodily system for facilitating drainage of a fluid from the first cavity to the second cavity; and a processor in communication with a memory and the sensor, the memory including instructions executable by the processor to:

access signal data indicative of the signal generated by the sensor;

compare the signal data to a behavioral model associated with the valve device, the behavioral model correlating the indirect operational characteristics of the valve device indicated by the signal data with a parametric behavior characteristic of the valve device with respect to the bodily system, wherein the behavioral model is based on in-vitro testing of the valve device and further based on correlations, from in-vivo testing of the valve device, between directly measured values of the parametric behavior characteristic and corresponding indirect operational characteristics of the valve device; and infer a value of the parametric behavior characteristic of the valve device based on a comparison between the signal data and the behavioral model.

2. The valve monitoring system of claim 1, wherein the indirect operational characteristics of the valve device include one or more of:

an opening time of the valve device associated with an opening action of the valve device over one or more cycles;

a closing time of the valve device associated with a closing action of the valve device over the one or more cycles; and a flow rate of the fluid through the valve device over the one or more cycles.

3. The valve monitoring system of claim 1, wherein the parametric behavior characteristics of the valve device include one or more of:

an intracavity pressure associated with the first cavity over one or more cycles;

a cracking pressure of the valve device; and a reverse flow rate associated with backflow of the fluid from the second cavity to the first cavity over the one or more cycles.

4. The valve monitoring system of claim 1, wherein the sensor is selected from:

an acoustic sensor that generates the signal upon audio detection of an opening action or a closing action of the valve device; and an ultrasound sensor that generates the signal expressive of the fluid flow through the valve device; and wherein the signal is readable by a computing system upon interrogation of the sensor.

5. The valve monitoring system of claim 1, the memory further including instructions executable by the processor to:

infer, based on the value of the parametric behavior characteristic of the valve device and based on the behavioral model, a type of operational state of the valve device.

6. The valve monitoring system of claim 1, the memory further including instructions executable by the processor to:

construct, based on the value of the parametric behavior characteristic of the valve device and based on the behavioral model, a graphic for display at a display device in communication with the processor that shows the indirect operational characteristics of the valve device and the value of the parametric behavior characteristic of the valve device with respect to time.

7. The valve monitoring system of claim 1, the memory further including instructions executable by the processor to:

infer, based on the value of the parametric behavior characteristic of the valve device and based on the behavioral model, a remaining lifetime of the valve device.

8. The valve monitoring system of claim 1, the memory further including instructions executable by the processor to:

correlate the indirect operational characteristics of the valve device over one or more cycles with a series of postural changes associated with the bodily system; and compare, in view of correlation between the indirect operational characteristics and the series of postural changes, the behavioral model correlating the indirect operational characteristics of the valve device indicated by the signal data with parametric behavior characteristics of the valve device with respect to the bodily system.

9. The valve monitoring system of claim 8, the memory further including instructions executable by the processor to:

prompt, by an interface in communication with the processor, a user of the valve device to perform the series of postural changes; and access the signal data indicative of the signal generated by the sensor upon performance of the series of postural changes.

10. A method of inferring a value of a parametric behavior characteristic that indicates function of a valve device using a behavioral model of the valve device, the method comprising:

accessing signal data indicative of a signal generated by a sensor, the signal being expressive of one or more indirect operational characteristics of a valve device, the valve device being positioned between a first cavity and a second cavity of a bodily system for facilitating drainage of fluid from the first cavity to the second cavity;

comparing the signal data to a behavioral model associated with the valve device, the behavioral model correlating the one or more indirect operational characteristics of the valve device indicated by the signal data with one or more parametric behavior characteristics associated with the valve device with respect to the bodily system, wherein the behavioral model is based on in-vitro testing of the valve device and further based on correlations, from in-vivo testing of the valve device, between directly measured values of the parametric behavior characteristic and corresponding indirect operational characteristics of the valve device; and inferring a value of a parametric behavior characteristic of the one or more parametric behavior characteristics associated with the valve device based on comparison between the signal data and the behavioral model.

11. The method of claim 10, wherein the one or more indirect operational characteristics of the valve device includes one or more of:

an opening time of the valve device associated with an opening action of the valve device over one or more cycles;

a closing time of the valve device associated with a closing action of the valve device over the one or more cycles; and a flow rate of fluid through the valve device over the one or more cycles.

12. The method of claim 10, wherein the one or more parametric behavior characteristics of the valve device includes one or more of:

an intracavity pressure associated with the first cavity over one or more cycles;

a cracking pressure of the valve device; and a reverse flow rate associated with backflow of fluid from the second cavity to the first cavity over the one or more cycles.

13. The method of claim 10, further comprising:

correlating the one or more indirect operational characteristics of the valve device over one or more cycles with a series of postural changes associated with the bodily system; and comparing, in view of correlation between the one or more indirect operational characteristics and the series of postural changes, the behavioral model correlating the one or more indirect operational characteristics of the valve device indicated by the signal data with parametric behavior characteristics of the valve device with respect to the bodily system.

14. A method of developing a behavioral model for use in inferring a value of a parametric behavior characteristic that indicates function of a valve device, comprising:

measuring, by a plurality of sensors associated with a valve device implanted within an animal bodily system over a plurality of cycles, a set of operational characteristics associated with the valve device including:

an intracavity pressure associated with a first cavity of the animal bodily system; and a set of indirect operational characteristics of the valve device, including timestamps associated with an opening action of the valve device or a closing action of the valve device over the plurality of cycles, and fluid flow through the valve device; and constructing a behavioral model for the valve device representing connections between the intracavity pressure and the set of indirect operational characteristics of the set of operational characteristics.

15. The method of claim 14, wherein the behavioral model expresses a correlation between the set of operational characteristics and a series of postural changes exhibited by the animal bodily system.

16. The method of claim 14, wherein the behavioral model incorporates an equivalent circuit behavioral model in terms of an equivalent circuit model of the valve device and the animal bodily system, the equivalent circuit behavioral model representing connections between one or more design parameters of the valve device, one or more bodily system parameters including intracavity pressure, and one or more equivalent circuit parametric behavioral characteristics of the valve device.

17. The method of claim 16, the method further comprising:

simulating operation of the equivalent circuit model of the valve device;

varying one or more bodily system parameters of the equivalent circuit model;

observing, based on simulated operation of the equivalent circuit model of the valve device, one or more equivalent circuit parametric behavioral characteristics of the equivalent circuit model responsive to variation of the one or more bodily system parameters; and correlating the one or more bodily system parameters of the equivalent circuit model with the one or more equivalent circuit parametric behavioral characteristics of the valve device of the equivalent circuit model.

18. The method of claim 16, wherein the behavioral model incorporates connections between the equivalent circuit behavioral model and the set of operational characteristics associated with the valve device and the animal bodily system.

19. The method of claim 14, wherein the behavioral model incorporates a testbed behavioral model in terms of a testbed model of the valve device and the animal bodily system, the testbed behavioral model representing connections between one or more design parameters of the valve device, one or more bodily system parameters including intracavity pressure, and one or more testbed parametric behavioral characteristics of the valve device based on the testbed model.

20. The method of claim 19, further comprising:

simulating operation of the testbed model of the valve device;

varying the one or more bodily system parameters of the testbed model;

measuring the one or more testbed parametric behavioral characteristics of the valve device of the testbed model responsive to variation of the one or more bodily system parameters; and correlating the one or more bodily system parameters of the testbed behavioral model with the one or more testbed parametric behavioral characteristics of the valve device of the testbed model.

* * * * *